US012773414B2

(12) United States Patent
Montoya Miñano et al.

(10) Patent No.: US 12,773,414 B2
(45) Date of Patent: Oct. 27, 2026

(54) STEROIDAL NITRONE F2 FOR USE IN THE PREVENTION AND/OR TREATMENT OF PERMANENT CEREBRAL ISCHAEMIA

(71) Applicants: ISQUAEMIA BIOTECH, S.L., Madrid (ES); FUNDACIÓN PARA LA INVESTIGACIÓN BIOMÉDICA DEL HOSPITAL RAMÓN Y CAJAL, Madrid (ES)

(72) Inventors: Juan José Montoya Miñano, Madrid (ES); Alberto Alcázar González, Madrid (ES); Emma Martínez Alonso, Madrid (ES); Daniel González Nieto, Pozuelo de alarcón (ES); Jose Luis Marco Contelles, Madrid (ES)

(73) Assignees: ISQUAEMIA BIOTECH, S.L., Madrid (ES); FUNDACIÓN PARA LA INVESTIGACIÓN BIOMÉDICA DEL HOSPITAL RAMÓN Y CAJAL, Madrid (ES)

( * ) Notice: Subject to any disclaimer, the term of this patent is extended or adjusted under 35 U.S.C. 154(b) by 574 days.

(21) Appl. No.: 17/909,278

(22) PCT Filed: Mar. 5, 2021

(86) PCT No.: PCT/EP2021/055653
§ 371 (c)(1),
(2) Date: Sep. 2, 2022

(87) PCT Pub. No.: WO2021/176085
PCT Pub. Date: Sep. 10, 2021

(65) Prior Publication Data

US 2023/0122393 A1 Apr. 20, 2023

(30) Foreign Application Priority Data

Mar. 5, 2020 (EP) .................................... 20382158

(51) Int. Cl.
*A61K 31/575* (2006.01)
*A61P 25/28* (2006.01)

(52) U.S. Cl.
CPC ............ *A61K 31/575* (2013.01); *A61P 25/28* (2018.01)

(58) Field of Classification Search
CPC .................................................... A61K 31/575
See application file for complete search history.

(56) References Cited

FOREIGN PATENT DOCUMENTS

EP 3000469 * 3/2016 ........... A61K 31/575

* cited by examiner

*Primary Examiner* — Paul V Ward
(74) *Attorney, Agent, or Firm* — Seed Intellectual Property Law Group LLP

(57) ABSTRACT

The present invention refers to steroidal nitrone (E)-N-((8S, 9S,10R,13R,14S,17R)-10,13-di methyl-17-(R)-6-methyl hepta n-2-yl)-7,8,9,11,12,13,14,15,16,17-deca hydro-1H-cyclopenta[a]phenanthren-3(2H,6H,10H)-ylidene)methanamine oxide (F2), as well as any pharmaceutically acceptable salt thereof, for use in the prevention and/or treatment of permanent cerebral ischemia.

5 Claims, 10 Drawing Sheets

STEROIDAL NITRONE F2 FOR USE IN THE PREVENTION AND/OR TREATMENT OF PERMANENT CEREBRAL ISCHAEMIA

TECHNICAL FIELD OF THE INVENTION

The present invention relates to the medical field, particularly to specific uses of a steroidal nitrone for the treatment and/or prevention of a cerebral stroke or ischaemia.

BACKGROUND OF THE INVENTION

Stroke represents the second largest cause of death worldwide. Being the ischemic subtype approximately 80% of the registered cases [1], it is caused by a decrease in cerebral blood flow affecting to the whole or part of the brain (global or focal cerebral ischemia, respectively). Reduction of blood flow that is usually originated by a thrombus or embolus occluding a blood vessel or by a systemic hypoperfusion in the brain. As a consequence of the decrease in blood supply, and modulated by its severity, duration, and area of the brain affected, diverse effects are triggered within the components of the neurovascular unit. This set of processes, also referred as the 'ischemic cascade', leads to the loss of cell functionality and, eventually, to the loss of cell integrity and death [2].

In the last decades, a plethora of strategies have been directed against different components of the ischemic cascade in order to find an adequate approach for the treatment of the ischemic disease, overcoming the limitations of recanalization therapies, i.e., the endovascular thrombectomy and intravenous thrombolysis with recombinant tissue plasminogen activator (rtPA), the only approved therapies for the treatment of ischemic stroke by US Food and Drug Administration (FDA). Either alone or in combination with other strategies, antioxidant therapy has long been considered an interesting field of research regarding oxidative stress' relevance in the ischemic episode [3]. Briefly, during the duration of the occlusion, but especially after the recanalization is produced, in which a massive flow of oxygen reaches the compromised tissue, an overproduction of highly reactive oxygen and nitrogen species takes place [4]. If uncontrolled by the endogenous antioxidant mechanisms, which are actually compromised as a consequence of the energy deprivation, radical species may further contribute to exacerbate the damage of the ischemia/reperfusion period. Antioxidant drugs are more often aimed to the scavenging of radical species (i.e. radical traps), to inhibit the enzymes producer of ROS/RNS, or to recover or increase the activity of the endogenous antioxidant systems (glutathione, SOD, etc.) [5].

Nitrones were initially developed as detection tools of radical species due to the formation of nitrone-radical adducts able to be observed by electron paramagnetic resonance methods [6]. In the following years and after the pathological role of free radicals was established for several diseases, nitrone radical trapping behaviour was suggested as a relevant feature in the fight against oxidative stress [7]. N-tert-Butyl-α-phenylnitrone (PBN), extensively studied in the analytical experiments, was reported to exert a protective effect on rats after traumatic head injury [8]. After some development, the PBN-derived nitrone NXY-059, with greater solubility than the parent compound, was described as a good neuroprotective agent in preclinical stages, which prompted its suggestion as a candidate for the treatment of ischemic stroke [9, 10]. Phase I and II studies revealed adequate pharmacokinetic characteristics and tolerability [11-13]. Phase III studies, however, were not able to show a conclusive beneficial effect when compared to placebo, fact that lead to NXY-059 withdrawal from the clinical trial path [14].

From that point, and despite NXY-059's lack of benefit in the clinical phases, nitrone development has remained as an appealing field of research in the search for new candidates for the treatment of ischemic stroke and other diseases. It is the connectivity, nature and position of the substituents on the nitrone group (the N-oxide of an imine) the main features modulating the chemical and pharmacological activity of nitrones. Thus, radical trapping activity can be easily modified with subtle chemical changes on the main scaffold, leading to more potent drugs. But, at the same time, this confers nitrones a great versatility that makes possible to find compounds not only able to act as radical traps, but also to exert other functions, as examples of pleiotropic drugs.

Drugs aimed for the treatment of ischemic stroke must feature precise characteristics, regarding stroke physiopathology, to increase the chances of success. Even in the best situations, patient arrival to the hospital, diagnose and start of treatment take several hours from the production of the occlusion. Treatments must, therefore, be effective and, of course, safe, in an extended time window covering the time period required before treatment, including the time required for recanalization—if not spontaneous.

Recent studies have also pointed out the relevance of long-term recovery in patients who have suffered a stroke. The average age of stroke incidence has dramatically decreased in the last years, mainly because of poorer lifestyles and accumulated risk factors in younger individuals [15]. Apart from the sequelae common to older patients, these young adults (i.e. younger than 50) may eventually develop compromised functional, neuropsychiatric or cardiovascular outcomes at long-term but still early in their life, conditioning their life expectancy [16]. Because of these reasons, long-term effect should also be a priority in the drug development process and, not only during the observation phase after drug approval, but it should also be considered during the preclinical development to bring to the clinic candidates that are selected precisely for their long-term effects.

Previously, the first insight into the biological activity of a cholesterol-derived nitrone (i.e., cholesteronitrone) as a potential treatment for ischemic stroke was reported [17]. F2 was identified in [17], as a promising candidate after it was administered to primary neuronal cultures subjected to oxygen and glucose deprivation (OGD) as a model of experimental ischemia. Cell viability studies revealed a good neuroprotective effect in the micromolar range that prompted us to explore F2 effect on an in vivo model of cerebral ischemia. Intraperitoneal administration of the candidate at the onset of reperfusion after cerebral ischemia afforded neuroprotective effect when compared to the vehicle group [17]. Regarding these promising results, we decided to continue exploring the biological and pharmacological properties of F2.

REFERENCES

1. World Health Organization. Global health estimates 2014 summary tables: deaths by cause, age and sex, 2000-2016. 2016
2. Moskowitz, M. A.; Lo, E. H.; Iadecola, C. The science of stroke: mechanisms in search of treatments. Neuron 2010, 67(2):181-198. DOI: 10.1016/j.neuron.2010.07.002.

3. Brouns, R.; De Deyn, P. P. The Complexity of Neurobiological Processes in Acute Ischemic Stroke. Clin Neurol Neurosurg 2009, 111, 483-495. DOI: 10.1016/j.clineuro.2009.04.001.
4. Rodrigo, R.; Fernández-Gajardo, R.; Gutiérrez, R.; Matamala, J. M.; Carrasco, R.; Miranda-Merchak, A.; Feuerhake, W. Oxidative stress and pathophysiology of ischemic stroke: novel therapeutic opportunities. CNS Neurol Disord Drug Targets 2013 12(5), 698-714. DOI: 10.2174/1871527311312050015.
5. Bach, A. Targeting Oxidative Stress in Stroke. In Neuroprotective Therapy for Stroke and Ischemic Disease; Lapchak, P. A., Zhang, H. J., Eds.; Springer: Cham, Switzerland, 2017; pp. 203-250. DOI: 10.1007/978-3-319-45345-3.
6. Iwamura, M.; Inamoto, N. Novel formation of nitroxide radicals by radical addition to nitrones. Bull Chem Soc Jpn 1967, 40(3), 703. DOI: 10.1246/bcsj.40.703.
7. Floyd, R. A.; Kopke, R. D.; Choi, C. H.; Foster, S. B.; Doblas, S.; Towner, R. A. Nitrones as therapeutics. Free Radic Biol Med 2008, 45(10), 1361-1374. DOI: 10.1016/j.freeradbiomed.2008.08.017.
8. Novelli, G. P.; Angiolini, P.; Tani, R.; Consales, G.; Bordi, L. Phenyl-t-butyl-nitrone is active against traumatic shock in rats. Free Radic Res Commun 1986, 1(5), 321-327. DOI: 10.3109/10715768609080971.
9. Green, A. R.; Ashwood, T.; Odergren, T.; Jackson, D. M. Nitrones as neuroprotective agents in cerebral ischemia, with particular reference to NXY-059. Pharmacol Ther 2003, 100, 195-214. DOI: 10.1016/j.pharmthera.2003.07.003.
10. Kuroda, S.; Tsuchidate, R.; Smith, M.-L.; Maples, K. R.; Siesjo, B. K. Neuroprotective Effects of a Novel Nitrone, NXY-059, After Transient Focal Cerebral lschemia in the Rat. J Cereb Blood Flow Metab 1999, 19, 778-787.
11. Edenius, C.; Strid, S.; Borgå, O; Breitholtz-Emanuelsson, A.; Vallén, K. L.; Fransson, B. Pharmacokinetics of NXY-059, a nitrone-based free radical trapping agent, in healthy young and elderly subjects. J Stroke Cerebrovasc Dis 2002, 11, 34-43. DOI: 10.1053/jscd.2002.123973.
12. Lees, K. R.; Sharma, A. K.; Barer, D.; Ford, G. A.; Kostulas, V.; Cheng, Y. F.; Odergren, T. Tolerability and pharmacokinetics of the nitrone NXY-059 in patients with acute stroke. Stroke 2001, 32(3), 675-680. DOI: 10.1161/01.str.32.3.675.
13. Lees, K. R.; Barer, D.; Ford, G. A.; Hacke, W.; Kostulas, V.; Sharma, A. K.; Odergren, T. Tolerability of NXY-059 at higher target concentrations in patients with acute stroke. Stroke 2003, 34(2), 482-487. DOI: 10.1161/01.str.0000053032.14223.81.
14. Lees, K. R.; Davalos, A.; Davis, S. M.; Diener, H.-C.; Grotta, J.; Lyden, P.; Shuaib, A.; Ashwood, T.; Hårdemark, H.-G.; Wasiewski, W.; Emeribe, U.; Zivin, J. A.; SAINT I Investigators. Additional outcomes and subgroup analyses of NXY-059 for acute ischemic stroke in the SAINT I trial. Stroke 2006, 37, 2970-2978. DOI: 10.1161/01.STR.0000249410.91473.44
15. Singh, R.; Chen, S.; Ganesh, A.; Hill M. D. Long-term neurological, vascular, and mortality outcomes after stroke. Int J Stroke 2018, 13(8), 787-796. DOI: 10.1177/1747493018798526.
16. Meyer, S.; Verheyden, G.; Brinkmann, N.; Dejaeger, E.; De Weerdt, W.; Feys, H.; Gantenbein, A. R.; Jenni, W.; Laenen, A.; Lincoln, N.; Putman, K.; Schuback, B.; Schupp, W.; Thijs, V.; De Wit, L. Functional and motor outcome 5 years after stroke is equivalent to outcome at 2 months: Follow-up of the collaborative evaluation of rehabilitation in stroke across Europe. Stroke 2015; 46, 1613-1619. DOI: 10.1161/STROKEAHA.115.009421.
17. Ayuso, M. I.; Chioua, M.; Martinez-Alonso, E.; Soriano, E.; Montaner, J.; Masjuán, J.; Hadjipavlou-Litina, D. J.; Marco-Contelles, J.; Alcázar, A. CholesteroNitrones for Stroke. J Med Chem 2015, 58, 6704-6709. DOI: 10.12021/acs.jmedchem.5b00755

DESCRIPTION OF THE INVENTION

Figure 1:
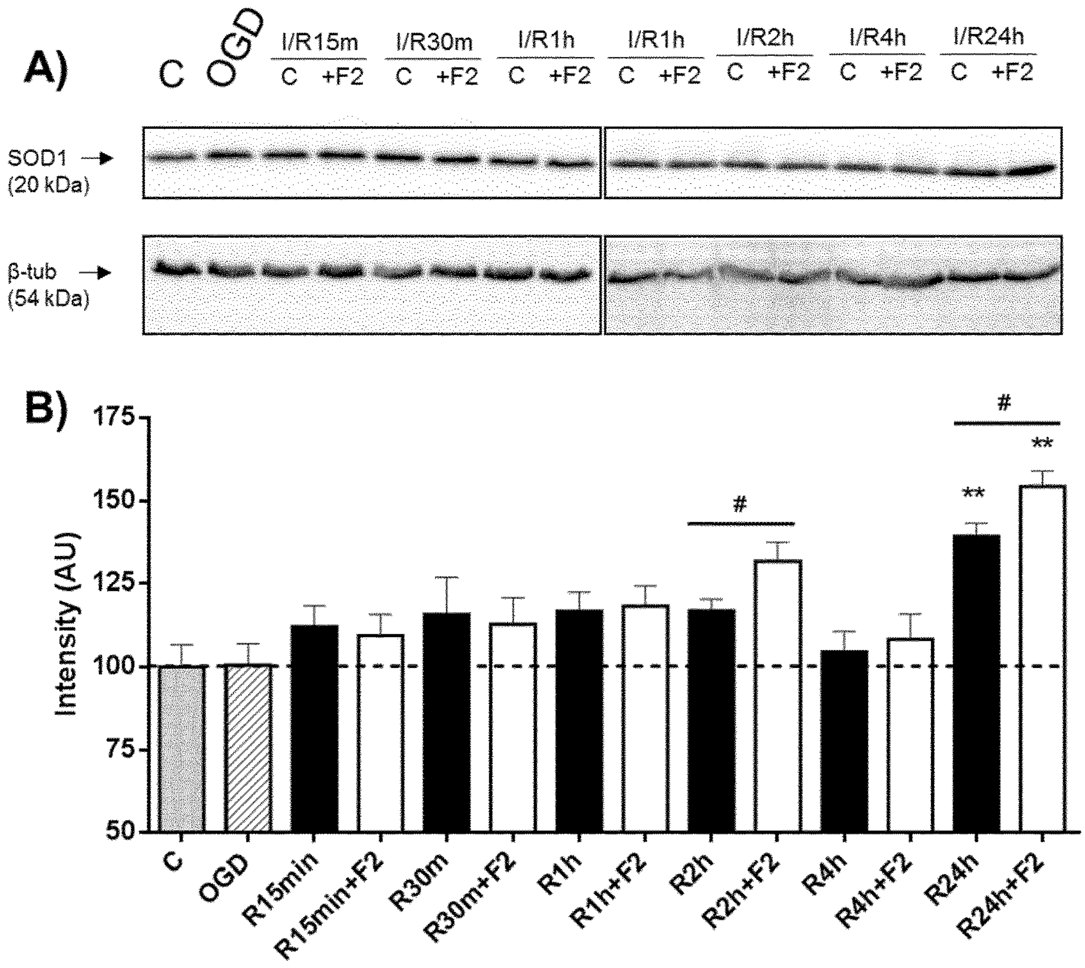
FIG. 1. Effect of F2 on SOD1 protein levels in primary neuronal cultures subjected to OGD and allowed to recover for 15 min, 30 min, 1 h, 2 h, 4 h and 24 h, as determined by western blot. (A) Representative blots. (B) SOD1 total protein levels. Results represent means±SEM. **$p<0.01$ compared with C-control group by ANOVA and Dunnett's post-test. #$p<0.05$ compared with untreated group by Student's t-test.

Currently, recanalization strategies, either pharmacological (e.g., rtPA) or endovascular treatment (thrombectomy), are the only approved therapies by the FDA or European Medicines Agency (EMA) for the treatment of acute ischemic stroke (AIS). A substance or therapeutic strategy able to minimize the damage produced after the ischemia-reperfusion injury is, therefore, highly needed, to use as single therapy or in combination with the previously mentioned recanalization approaches. To date, despite the extensive research in the area, no substance has been found effective in improving patient's outcomes or decreasing the stroke-associated mortality.

A nitrone compound, F2, which was previously reported (Ayuso, M. I.; Chioua, M.; Martinez-Alonso, E.; Soriano, E.; Montaner, J.; Masjuán, J.; Hadjipavlou-Litina, D. J.; Marco-Contelles, J.; Alcázar, A. Cholestero Nitrones for Stroke. J Med Chem 2015, 58, 6704-6709. DOI: 10.12021/acs.jmedchem.5b00755), was able to exert a neuroprotective effect over primary neuronal cultures subjected to oxygen and glucose deprivation. Also, preliminary results were reported regarding F2 effect on lipid peroxidation and ROS levels, which were both decreased. Intraperitoneal administration of F2 at the onset of reperfusion after global cerebral ischemia showed decreased neuronal death and apoptosis in those regions more vulnerable to the ischemia-reperfusion period—i.e. hippocampus and cortex. Regarding these findings, F2 was upgraded as a lead in the treatment of AIS.

For this invention an updated biological and pharmacological characterization of F2 as a preclinical candidate for AIS treatment was performed. Here, we have evaluated the efficacy of different doses of F2 (0.01-0.1 mg/kg) administered by intravenous injection in an in vivo model of cerebral ischemia. This study identified 0.05 mg/kg as the most effective dose in decreasing neuronal death and apoptosis at 5 days after reperfusion. This low dose would decrease the probability of adverse effects due to off-target activity, as well as reduce toxicity concerns.

The acute character of stroke disease makes the time period between onset of stroke—or appearance of symptoms—and administration of treatment a crucial concern in the development of potential therapies and health systems strategies. Commonly, several hours pass between the development of the first symptoms and diagnosis and administration of a treatment. Besides, if not spontaneously produced, patients may require a recanalization treatment, which may also determine the effect of additional drugs used. Therefore, the study of the effectivity of a potential treatment in a delayed administration basis must be explored in preclinical models of ischemia to properly assess its safety, therapeutic effect and potential suitability for the clinic.

Considering the relevance of a delayed administration schedule in the common clinical practice, the effectivity of a single F2 administration has also been explored in a time window ranging from 0 to 48 h after reperfusion onset. Results reported here confirm the effectivity of F2 in decreasing neuronal death, neuronal apoptosis and general neurofunctional deficits in our preclinical model when administered even 6 h after stroke. Even though compatibility of these results with recanalization strategies is still unknown, and correlation with administration time points in human patients must still be assessed, the feature of F2 is of paramount relevance and could be decisive in its further development. Whether an antioxidant activity—theoretically most effective when administered shortly after the recanalization—is the cause of the effectivity found at such long time periods after the reperfusion onset, must be explored in further studies.

Increasing life expectancy and earlier incidence of stroke episodes requires the assessment of different outcomes at longer time periods, both in clinical and preclinical phases. Being conscious of the obvious limitations trying to compare life spans between different species, a 3-month-long post-treatment period in adult rats has been explored, which would correspond to a 5-7 years life span in humans. Regardless of the exact equivalence between the two species, this time period allows the observation of the evaluation parameters once the brain remodelling action after the injury has been completed or, in other words, when the endogenous neurorepair processes have already finished. Therefore, the biochemical analysis and neurofunctional tests to perform must be able to assess the permanent sequelae that could have resulted from the ischemic episode. The immunofluorescence detection of S6 protein 11 weeks (3 months) after the onset of reperfusion has allowed the observation of the anatomical disruption produced in the hippocampal CA1 region resulting from the ischemic injury. Behavioural tests confirmed this by detecting an impaired performance in the spontaneous spatial recognition and spatial memory tests in untreated ischemic animals. Remarkably, F2 treatment not only avoided short term deleterious effects, as seen previously in the TUNEL and Fluoro-Jade B experiments at 5 days of reperfusion, but also decreased the long-term functional impairment at a 3-month-long period.

Furthermore, F2 was assayed in another species and another experimental model of cerebral ischemia, a transient focal ischemia model. F2 decreased the functional motor deficit, and, notably, produced a reduction in the infarct size in the animals subjected to transient focal ischemia. In addition, and remarkably, we have further identified, as reflected in example 1, that compound F2 was capable of significantly increase the levels of SOD1 (superoxide dismutase 1), a protein that was increased by F2 at 2 and 24 hours after inducing an ischemic condition. In accordance with these results, F2 can promote neuroprotection in two ways, by increasing SOD1 expression, i) initially (2 h) enhancing the antioxidant capacity of neurons, and later (24 h) by ii) increasing the capacity to reinforce cellular repair.

Based on the above results, the present invention describes, for the first time, new specific uses of steroidal nitrone (E)-N-((8S,9S,10R,13R,14S,17R)-10,13-dimethyl-17-((R)-6-methylheptan-2-yl)-7,8,9,11,12,13,14,15,16,17-decahydro-1H-cyclopenta[a]phenanthren-3(2H,6H,10H)-ylidene)methanamine oxide (F2) (details on the synthesis of this specific compound can be found on EP3000469 (B1)). In particular, a first aspect of the invention refers to the steroidal nitrone (E)-N-((8S,9S,10R,13R,14S,17R)-10,13-dimethyl-17-((R)-6-methylheptan-2-yl)- 7,8,9,11,12,13,14,15,16,17-decahydro-1H-cyclopenta[a]phenanthren-3(2H,6H,10H)-ylidene)methanamine oxide (F2), as well as any pharmaceutically acceptable hydrates, salts, and polymorphs thereof, for use in promoting neuroprotection in a subject in need thereof by increasing SOD1 expression, initially enhancing the antioxidant capacity of neurons, and later by increasing this capacity to reinforce cellular repair. Such effect, as illustrated in example 6, aids in F2 significantly reducing infarct volume in F2-treated animals with permanent cerebral ischemia. In fact, the neuroprotective effect of F2 provided a higher functional preservation of the cortical territory examined by the recordings of the somatosensory evoked potentials, effect that could be still observed after three weeks of F2 treatment. Therefore, a second aspect of the invention refers to the steroidal nitrone (E)-N-((8S,9S,10R,13R,14S,17R)-10,13-dimethyl-17-((R)-6-methylheptan-2-yl)-7,8,9,11,12,13,14,15,16,17-decahydro-1H-cyclopenta[a] phenanthren-3(2H,6H,10H)-ylidene)methanamine oxide (F2), as well as any pharmaceutically acceptable hydrates, salts, and polymorphs thereof, for use in the prevention and/or treatment of permanent cerebral ischemia in a subject in need thereof.

In a preferred embodiment of the second aspect of the invention, the steroidal nitrone F2, as well as any pharmaceutically acceptable hydrates, salts, and polymorphs thereof, for use in the prevention and/or treatment of permanent cerebral ischemia in a subject in need thereof, is administered between the onset of reperfusion (either produced spontaneously or pharmacologically induced) and 6 h after. As indicated in example 7, such administration induced a significant decrease of neuronal death and neuronal apoptosis, as well as an improvement in the neurological deficit, when compared with the damage produced by cerebral ischemia in both untreated and NXY-059-treated animals. Preferably, F2 is administered within a therapeutic window starting by the reperfusion onset until 6 h after reperfusion, preferably between 0 and 3 h after reperfusion, preferably between 1 and 6 h after reperfusion, preferably between 2 and 6 h after reperfusion, preferably between 3 and 6 h after reperfusion, preferably between 4 and 6 h after reperfusion, preferably between 5 and 6 h after reperfusion.

In the context of the present invention, "permanent cerebral ischemia" is herein understood as a decrease in cerebral blood flow affecting to the whole or part of the brain (global or focal cerebral ischemia, respectively), which does not recover spontaneously or induced by a treatment.

In a preferred embodiment of the second aspect of the invention, the steroidal nitrone F2 is comprised in a composition, preferably in a pharmaceutical composition, wherein, more preferably, such composition further comprises a thrombolytic agent and/or, optionally, pharmaceutically suitable excipients, and wherein preferably said thrombolytic agent is tissue plasminogen activator (rtPA) or recombinant tissue plasminogen activator (rtPA).

In another preferred embodiment of the second aspect of the invention, the steroidal nitrone F2 is use in adjuvant therapy administered simultaneously, alternatively or successively with respect to a first-line therapy for the treatment of permanent cerebral ischemia, wherein said first-line therapy is preferably a thrombectomy. Preferably, the steroidal nitrone F2 is use in adjuvant therapy administered successively with respect to a first-line therapy for the treatment of permanent cerebral ischemia, wherein said first-line therapy is preferably a thrombectomy. More preferably, the F2 adjuvant therapy is administered within a therapeutic window starting by the administration of the first-line therapy until 6 h after said administration, preferably between 0 and 3 h after said administration, preferably between 1 and 6 h after said administration, preferably between 2 and 6 h after said administration, preferably between 3 and 6 h after said administration, preferably between 4 and 6 h after said administration, preferably between 5 and 6 h after said administration.

In another preferred embodiment of the second aspect of the invention, the steroidal nitrone F2 is use in adjuvant therapy administered simultaneously, alternatively or successively with respect to a thrombolytic agent suitable for the treatment of permanent cerebral ischemia, wherein preferably said thrombolytic agent is tissue plasminogen activator (rtPA) or recombinant tissue plasminogen activator (rtPA). Preferably, the steroidal nitrone F2 is use in adjuvant therapy administered successively with respect to rtPA therapy for the treatment of permanent cerebral ischemia. More preferably, the F2 adjuvant therapy is administered within a therapeutic window starting by the administration of the rtPA therapy until 6 h after said administration, preferably between 0 and 3 h after said administration, preferably between 1 and 6 h after said administration, preferably between 2 and 6 h after said administration, preferably between 3 and 6 h after said administration, preferably between 4 and 6 h after said administration, preferably between 5 and 6 h after said administration.

In another preferred embodiment of the second aspect of the invention, the steroidal nitrone F2 is use in adjuvant therapy administered simultaneously, alternatively or successively with respect to a thrombectomy.

Thirdly, it is further noted, that the effect described in the first aspect of the invention and as illustrated in example 5, further results in that treatment with F2, in a transitory focal cerebral ischemia model, decreases the loss of motor function when compared to vehicle treatment in the functional test. In addition, treatment with F2 significantly reduces infarct volume when compared to vehicle and to NXY-059 treatment. Therefore, a third aspect of the invention, refers to the steroidal nitrone (E)-N-((8S,9S,10R,13R,14S,17R)-10,13-dimethyl-17-((R)-6-methylheptan-2-yl)-7,8,9,11,12,13,14,15,16,17-decahydro-1H-cyclopenta[a]phenanthren-3(2H,6H,10H)-ylidene)methanamine oxide (F2), as well as any pharmaceutically acceptable hydrates, salts, and polymorphs thereof, for use in the prevention and/or treatment of transitory, optionally focal, cerebral ischemia in a subject in need thereof.

In the context of the present invention, "transitory cerebral ischemia" is herein understood as a decrease in cerebral blood flow affecting to the whole or part of the brain (global or focal cerebral ischemia, respectively), which is restored spontaneously or induced by a treatment.

In a preferred embodiment of the third aspect of the invention, the steroidal nitrone F2 is comprised in a composition, preferably in a pharmaceutical composition, wherein, more preferably, such composition further comprises a thrombolytic agent and/or, optionally, pharmaceutically suitable excipients, and wherein preferably said thrombolytic agent is tissue plasminogen activator (rtPA) or recombinant tissue plasminogen activator (rtPA).

In another preferred embodiment of the third aspect of the invention, the steroidal nitrone F2 is use in adjuvant therapy administered simultaneously, alternatively or successively with respect to a first-line therapy for the treatment of transitory, optionally focal, cerebral ischemia, wherein said first-line therapy is preferably a thrombectomy.

In another preferred embodiment of the third aspect of the invention, the steroidal nitrone F2 is use in adjuvant therapy administered simultaneously, alternatively or successively with respect to a thrombolytic agent suitable for the treatment of transitory, optionally focal, cerebral ischemia, wherein preferably said thrombolytic agent is tissue plasminogen activator (rtPA) or recombinant tissue plasminogen activator (rtPA).

In another preferred embodiment of the third aspect of the invention, the steroidal nitrone F2 is use in adjuvant therapy administered simultaneously, alternatively or successively with respect to a thrombectomy.

Figure 5:
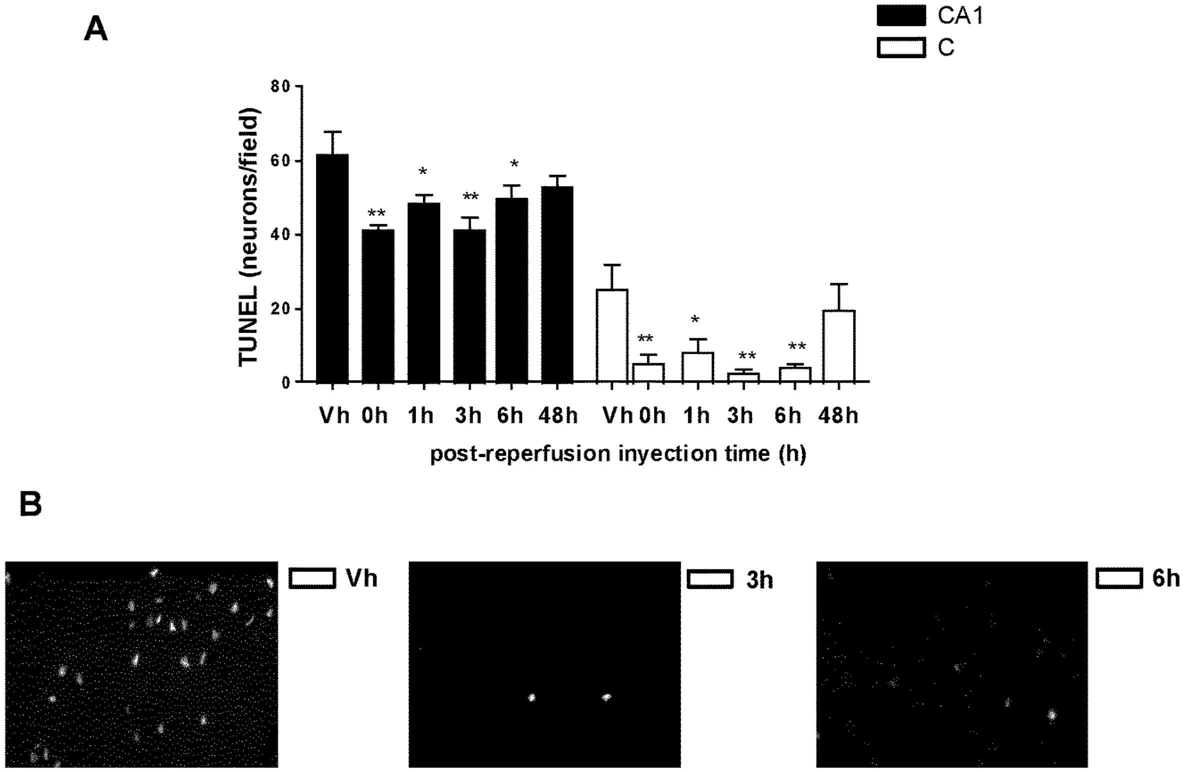
FIG. 5. Therapeutic window of steronitrone F2. (A) The figure shows the therapeutic window of the neuroprotective effect of F2. Brain sections from untreated (vehicle, Vh) or F2 (0.05 mg/kg) treated ischemic animals were used for neuroprotection evaluation. Animals were treated with F2 by an intravenous injection at the onset of reperfusion period (Oh) or at 1 h, 3 h, 6 h or 48 h of reperfusion after cerebral ischemia. Neuroprotection was determined by quantification of the decrease of neuronal apoptosis at 5 days after reperfusion following ischemia in the cerebral cortex (white bars) and in the hippocampal region CA1 (black bars). (B) Neuronal apoptosis was detected by TUNEL assay and visualized by fluorescence microscopy (in green). The images are representative results of the cerebral cortex from untreated (Vh) or F2 treated (0.05 mg/kg) animals at 3 h or 6 h of reperfusion after ischemia. F2 induced a significant neuroprotective effect when administered at 1-6 h of reperfusion after cerebral ischemia.
Figure 6:
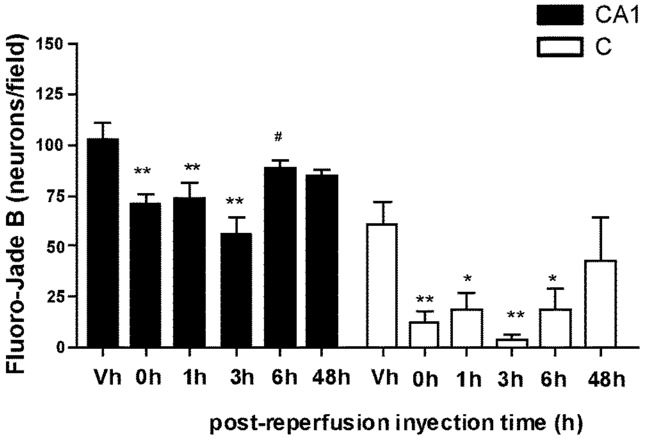
FIG. 6. Analysis of neuronal death. This figure represents the neuronal death quantified in brain sections (as in FIG. 5) from vehicle- and F2-treated animals after fixation and staining with Fluoro-Jade B. Neuroprotection was determined by quantification of the decrease of neuronal death in the hippocampal CA1 (CA1, black bars) and cortical (C, white bars) regions.

Lastly, it is further noted, that the effect described in the third aspect of the invention and as illustrated in example 3, further results in that treatment with steronitrone F2, administered between the onset of the reperfusion and 6 h after the cerebral ischemia, induces a significant decrease of neuronal damage and death, as well as an improvement in the neurological deficit, when compared to the damage produced by cerebral ischemia. In fact, compound F2 induces a neuroprotective effect when administered within a therapeutic window starting by the reperfusion onset until 6 h after reperfusion. In FIGS. 5 and 6, it can be observed that although the maximum neuroprotective effect is achieved when F2 is administered 0-3 h after reperfusion onset, this effect is still present when F2 is administered at 6 h of reperfusion. Therefore, a fourth aspect of the invention refers to the steroidal nitrone (E)-N-((8S,9S,10R,13R,14S,17R)-10,13-dimethyl-17-((R)-6-methylheptan-2-yl)-7,8,9,11,12,13,14,15,16,17-decahydro-1H-cyclopenta[a]phenanthren-3(2H,6H,10H)-ylidene)methanamine oxide (F2), as well as any pharmaceutically acceptable hydrates, salts, and polymorphs thereof, for use in the prevention and/or treatment of cerebral ischemia, preferably transitory cerebral ischemia, in a subject in need thereof, wherein said steroidal nitrone F2 is administered within a therapeutic window starting by the reperfusion onset until 6 h after reperfusion, preferably between 0 and 3 h after reperfusion, preferably between 3 and 6 h after reperfusion, preferably between 4 and 6 h after reperfusion, preferably between 5 and 6 h after reperfusion.

In a preferred embodiment of the fourth aspect of the invention, the steroidal nitrone F2 is comprised in a composition, preferably in a pharmaceutical composition, wherein, more preferably, such composition further comprises a thrombolytic agent and/or, optionally, pharmaceutically suitable excipients, and wherein preferably said thrombolytic agent is tissue plasminogen activator (rtPA) or recombinant tissue plasminogen activator (rtPA).

In another preferred embodiment of the fourth aspect of the invention, the steroidal nitrone F2 is use in adjuvant therapy administered simultaneously, alternatively or successively with respect to a first-line therapy for the treatment of cerebral ischemia, preferably transitory cerebral ischemia, wherein said first-line therapy is preferably a thrombectomy. Preferably, the steroidal nitrone F2 is use in adjuvant therapy administered successively with respect to a first-line therapy for the treatment of transitory cerebral ischemia, wherein said first-line therapy is preferably a thrombectomy. More preferably, the F2 adjuvant therapy is administered within a therapeutic window starting by the administration of the first-line therapy until 6 h after said administration, preferably between 0 and 3 h after said administration, preferably between 1 and 6 h after said administration, preferably between 2 and 6 h after said administration, preferably between 3 and 6 h after said administration, preferably between 4 and 6 h after said administration, preferably between 5 and 6 h after said administration.

In another preferred embodiment of the fourth aspect of the invention, the steroidal nitrone F2 is use in adjuvant therapy administered simultaneously, alternatively or successively with respect to a thrombolytic agent suitable for the treatment of cerebral ischemia, preferably transitory cerebral ischemia, wherein preferably said thrombolytic agent is tissue plasminogen activator (rtPA) or recombinant tissue plasminogen activator (rtPA). Preferably, the steroidal nitrone F2 is use in adjuvant therapy administered successively with respect to rtPA therapy for the treatment of transitory cerebral ischemia. More preferably, the F2 adjuvant therapy is administered within a therapeutic window starting by the administration of the rtPA therapy until 6 h after said administration, preferably between 0 and 3 h after said administration, preferably between 1 and 6 h after said administration, preferably between 2 and 6 h after said administration, preferably between 3 and 6 h after said administration, preferably between 4 and 6 h after said administration, preferably between 5 and 6 h after said administration.

In another preferred embodiment of the fourth aspect of the invention, the steroidal nitrone F2 is use in adjuvant therapy administered simultaneously, alternatively or successively with respect to a thrombectomy.

The following examples merely illustrate but do not limit the present invention.

EXAMPLE 1

Study of the Mechanism of Action of Cholesteronitrone F2

Materials and Methods

Primary Neuronal Cultures. Primary neuronal cultures from rat cerebral cortex were prepared as previously described in Alázar A., et al., 1997 J Neurochem 69, 1703-1708. All procedures associated with animal experiments were approved by the Ethics Committee of the Hospital Ramón y Cajal (Spain). Cell suspensions from cerebral cortex were prepared from 16- to 17-day-old Sprague-Dawley rat embryos. Living cells in cell suspension were counted by trypan blue exclusion method. Cells were seeded on plastic multidishes precoated with 0.05 mg/mL poly-D-lysine at a density of 2.5×105 cells/cm2 and were kept at 37° C. in a 6.5% CO2 atmosphere in high glucose Dulbecco's medium supplemented with 15% heat-inactivated (56° C. for 30 min) foetal calf serum. After 24 h, cultured cells were placed and kept in serum-free medium (Dulbecco's: Ham's F12, 1:1 [vol/vol], 5 mg/mL glucose, 2 mM L-glutamine, and 1 mM sodium pyruvate, and supplemented with 100 μg/mL transferrin, 100 μM putrescine, 20 nM progesterone, 30 nM sodium selenite, and 5 μg/mL insulin), as described by Bottenstein and Sato. 20 Six- to eight-day cultures were used in the experiments and contained 90% β-III tubulin-positive mature neurons.

An in vitro ischemia model within the hypoxia chamber was performed in these cultures, and subsequent reoxygenation and normoglycemia.

Exposure of Cell Cultures to Oxygen—Glucose Deprivation. Primary neuronal cultures were exposed to oxygen—glucose deprivation to induce experimental ischemia according to the protocol described in Chioua et al., 2012 J. Med. Chem. 55, 153-168. Cultured cells were washed and placed in glucose-free Dulbecco's medium (bubbled with 95% N2/5% CO2 for 30 min) and maintained in an anaerobic chamber containing a gas mixture of 95% N2/5% CO2 and humidified at 37° C. at a constant pressure of 0.15 bar. Cells were subjected to oxygen deprivation (<0.1%) and glucose (OGD) for 4 h (OGD 4 h), and then culture medium was replaced with oxygenated and normoglycemic serum-free medium, and cells were placed and maintained in the normoxic incubator for 15 minutes to 24 h to recovery (R15, R24 h). Control neurons cultured in Dulbecco's medium containing glucose were kept in the normoxic incubator for the same period of time as the OGD, and then culture medium was replaced with serum-free medium and cells were returned to the normoxic incubator until the end of recovery period. Control experiments included the same amounts of vehicle (final concentration <0.1% ethanol). F2 was added at the onset of recovery period. The experimental procedures were blindly performed, assigning a random order to each assayed nitrone. F2 were analysed independently from 4 to 8 times with different batches of cultures, and each experiment was run in quadruplicate.

Western Blotting 35-50 μg of protein cell extracts was resolved in 10 or 12% SDS-PAGE and blotted into a polyvinylidene difluoride (PVDF) membrane (GE Healthcare). Membranes were blocked with 5% (w/v) Blotto® (GE Healthcare) or with 2% (w/v) Prime® (GE Healthcare) blocking agent in TBST (50 mM Tris, pH 8.0; 150 mM NaCl; 0.5% Tween 20) for 90 or 60 min, respectively, and incubated with antibodies against SOD1 (Santa Cruz Biotechnologies) or β-tubulin (Sigma) at 4° C. overnight. Then, membranes were incubated with horseradish peroxidase-conjugated secondary antibodies for 1 h, developed with the ECL-Clarity (Bio-Rad) or Prime systems (GE Healthcare) and detected in a ChemiDoc imager (Bio-Rad).

For reproving, membranes were stripped in ReBlot Plus Strong Antibody Stripping Solution (Millipore), for 30 min at room temperature, washed with TBST and blocked again. The images were quantified using the quantification software ImageLab and Quantity One (Bio-Rad Laboratories). The protein levels were expressed as intensities in arbitrary units (AU).

Results

The main antioxidant cellular system in the central nervous system is the superoxide dismutase, an enzyme that exists in both cytoplasmic and mitochondrial subcellular localization. Mechanism of action studies were addressed by detecting differential levels of superoxide dismutase 1 (SOD1, cytoplasmic) involved in the cellular anti-oxidative processes. They were determined by analysing by western blot analysis on cytoplasmic extracts of cell cultures subjected to OGD and recovered in normoxic conditions for 15 min, 30 min, 1 h, 2 h, 4 h or 24 h, either treated or untreated with 5 μM F2. Non-OGD-treated cells served as control group. Results are shown in FIG. 1.

As can be seen in the above-mentioned figure, very constant levels of SOD1 were seen in the untreated groups throughout the study. OGD alone did not have an effect on SOD1 levels 2 h after induction of OGD but it caused an increase in SOD1 levels at 24 h (p=0.0018, ANOVA and Dunnett's post-test) after induction of OGD when compared to the control (no OGD). Surprisingly, presence of 5 μM F2 caused a significant increase of SOD1 levels at 2 h after OGD and enhanced the increase caused by OGD alone by 15% at 24 h (p=0.0208, t-test) after induction in comparison with the untreated and control groups.

Conclusions

Unexpectedly, compound F2 significantly increased the levels of the SOD1 2 and 24 hours after the ischemic condition. Importantly, F2 behaved as an activator of the endogenous antioxidant system. In accordance with these results, F2 can promote neuroprotection in two ways by increasing SOD1 expression, initially i) enhancing the antioxidant capacity of neurons, and later by ii) increasing the capacity to reinforce cellular repair.

EXAMPLE 2

Dose-Response Study of Cholesteronitrone F2 in an In Vivo Model of Transitory Global Cerebral Ischemia Materials and Methods Animal model of global cerebral ischemia, experimental design and administration of nitrones. Transient forebrain ischemia was induced in adult male Wistar rats (10-12 weeks, Charles River) by the standard four-vessel occlusion model (4VO) previously described. Briefly, both vertebral arteries were irreversibly occluded by electrocoagulation under anaesthesia with a mixture of atropine, ketamine and diazepam (0.25, 62.5, and 5 mg/kg, respectively) administered by intraperitoneal injection. After 24 h, ischemia was induced by carotid occlusion with atraumatic clips for 15 min and then clips were removed from the carotid arteries to allow reperfusion. Body temperature of 37° C. was maintained. Animals were studied at 5 days after reperfusion (R5d). A power analysis was performed (http://www.biomath.info/power/ttest.htm) to determine the sample size. The level of statistical significance was fixed at 0.05, the power set at 0.8 (80%), and the sample size obtained was <6 subjects per group. The treatments were performed with allocation concealment, assigning a random order to each vehicle or treated animal by a computer-generated randomization program. Ischemic animals were treated with nitrone F2 diluted in 10% ethanol in saline as vehicle by intravenous injection in the tail when the carotid arteries were unclamped for reperfusion. Vehicle-treated control animals were handled in the same way as treated animals. An independent investigator prepared the treatments for each animal according to the randomization schedule. All procedures associated with animal experiments were approved by The Ethics Committee of the Hospital Ramon y Cajal, Madrid, Spain, and performed according to ARRIVE guidelines.

Evaluation of neurological deficits. Neurological deficits in rats subjected to global cerebral ischemia were blindly evaluated using a scale previously described (Ayuso et al. 2015 J. Med. Chem. 58, 6704-6709; 10.1021/acs.jmedchem.5b00755). Evaluation of the overall neurological deficit score (NDS), including a score of general deficits and subscores in movement and sensory assessment, range from 0 (best) to 10 (rats had a depressed level of consciousness) and was validated in an entire cohort of R5d animals (n=20).

Brain sections. After 5 days after reperfusion, R5d animals were killed by transcardiac perfusion performed under deep anaesthesia. Perfusion via left ventricle was started with a washout of 200 mL of 0.9% NaCl, and the brains, following perfusion and fixation with 4% (w/v) paraformaldehyde solution in PBS, were removed and postfixed in the same solution overnight at 4° C. Brains were washed sequentially with 10, 20 and 30% (w/v) saccharose in PBS, embedded in Tissue-Tek O.C.T. (Sakura Finetek) and frozen at −80° C. prior to cryostat sectioning. Brain coronal sections containing the hippocampus were prepared at the level of interaural +5.7±0.2 mm on Real Capillary Gap microscope slides (Dako).

Neuronal death evaluation. Neuronal death was evaluated by Fluoro-Jade-B staining. Brain cryosections (10 μm thick) from ischemic animals that underwent reperfusion for 5 days were used after fixation to detect neuronal death by Fluoro-Jade-B staining (Ayuso et al. 2015 J. Med. Chem. 58, 6704-6709; 10.1021/acs.jmedchem.5b00755) and visualized by fluorescence microscopy. Labelled (dead) neuronal cells (in green) were counted as in TUNEL assay (see below). Data from different animals of each experimental group were independently analysed by two observers, and treatment information was blindly performed throughout the study.

TUNEL assay. Apoptotic neurons within brain sections were detected using the Terminal deoxynucleotidyl transferase-mediated dUTP Nick-End Labeling (TUNEL) assay (Promega). For this test, 5-μm-thick coronal cryostat brain sections containing the dorsal hippocampal formation were obtained as described above and post-fixed with 4% formaldehyde in PBS for 5 min at room temperature. After washing in PBS for three times, sections were permeabilized with 0.1 M sodium citrate, pH 6.0, for 1 min at 95° C., quickly cooled in ice and washed in PBS for 5 min at room temperature. Then, brain sections were incubated with blocking solution (0.1 M Tris-HCl, pH 7.5, 3% bovine serum albumin and 20% fetal bovine serum), washed in PBS for 5 min, and post-fixed with 4% formaldehyde in PBS for 5 min. After washing in PBS for three times, sections were incubated with buffer kit for 10 min, and then incubated with terminal deoxynucleotidyl transferase (TdT) and fluorescein-12-dUTP for 1.5 h at 37° C. as described by the supplier. The reaction was stopped by extensive washing in saline-sodium citrate buffer (30 mM sodium citrate in 0.3 M NaCl) at room temperature. After washing in PBS for three times, sections were then mounted with coverslips in anti-fade solution with glycerol-buffer containing p-phenylenediamine and 30 μM bisbenzimide (Hoechst 33342) for nuclear staining.

The hippocampal CA1 subfield and cerebral and lateral cortex fields from a given section were analysed with fluorescence microscopy (40× objective) to count the number of apoptotic nuclei (green). A grid of 330×220 μm2 was used to count the cells in the regions of interest and digitized with a colour CCD camera (1280×960-pixel resolution). TUNEL-positive cells were counted by two independent observers with a total area of 1.017 mm2 per section analysed. Four sections per brain sample were averaged per experiment and treatment information was kept concealed throughout the study.

Results

Results of the dose-response assay (concentration curve) of compound F2 administered by intravenous injection at reperfusion onset (immediately after reperfusion). Results obtained for the damage and neuronal death are described below. Data was obtained 5 d after post-ischemic reperfusion in a model of global ischemia.

Analysis of Neuronal Death

Figure 2:
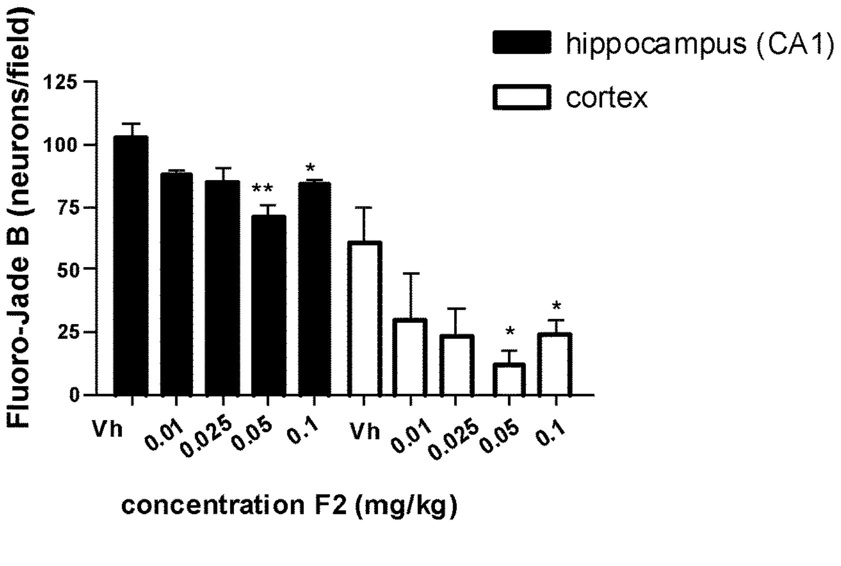
FIG. 2. In this figure, administered concentrations of compound F2 are shown as mg of F2 per kg of animal weight. Saline was used as vehicle control (Vh), meaning administration of 0.0 mg/kg F2.

Blood supply cessation in the global ischemia model during 15 min induces neuronal death, especially in the hippocampal CA1 and cortical regions of the brain. This neuronal damage can be observed at 5 days after reperfusion following ischemia by Fluoro-Jade B staining, as a marker of dead neurons. In these experiments, neuronal damage induced by ischemia is proportional to the number of cells stained with Fluoro-Jade B (FJB). In FIG. 2, administered concentrations of compound F2 are shown as mg of F2 per kg of animal weight. Saline was used as vehicle control (Vh), meaning administration of 0.0 mg/kg F2.

Analysis of Neuronal Apoptosis

Figure 3:
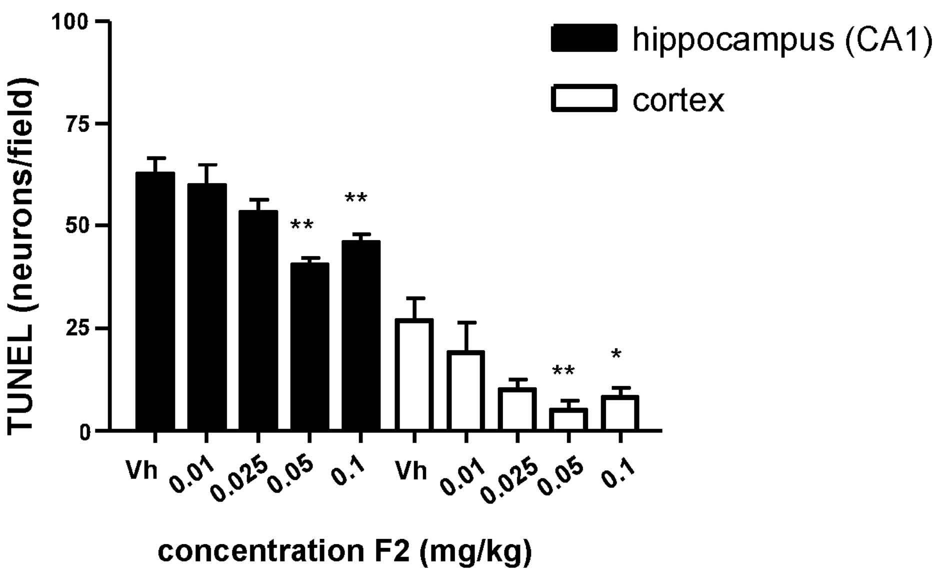
FIG. 3. In this figure, administered concentrations of compound F2 are shown as mg of F2 per kg of animal weight. Saline was used as vehicle control (Vh), meaning administration of 0.0 mg/kg F2.

Neuronal apoptosis can be observed as a consequence of the 15-min-long global ischemia when brain slices are subjected to TUNEL assay at 5 days after reperfusion following ischemia, as described in the Materials and Methods section. Cortical and, especially, hippocampal CA1 regions are the most vulnerable to the blood flow impairment in this experimental model, being therefore adequate for the observation of potential neuroprotective effects. Results shown in FIG. 3 describe the neuronal death induced by ischemia observed by staining of apoptosis-positive cells in the TUNEL assay, whose number is proportional to the damage induced by the ischemic episode. In this figure, administered concentrations of compound F2 are shown as mg of F2 per kg of animal weight. Saline was used as vehicle control (Vh), meaning administration of 0.0 mg/kg F2.

Dose-Response Curve

Figure 4:
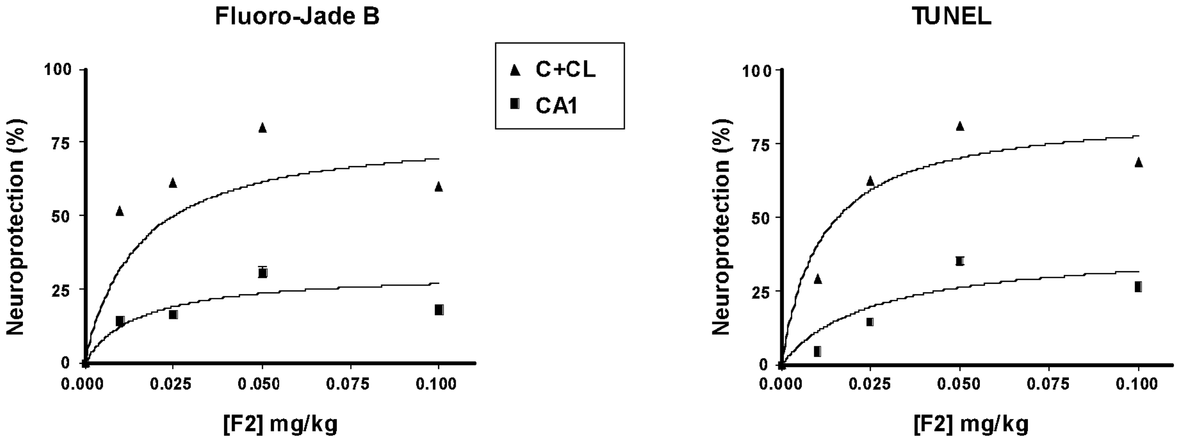
FIG. 4. Dose-response curve of steronitrone F2. The figure shows the dose-response curve of the neuroprotective effect of F2. Neuroprotection was determined by quantification of the neuronal death and apoptosis detected by Fluoro-Jade B and TUNEL assay, respectively, at 5 days of reperfusion after ischemia in the cerebral cortex (triangles) and in the hippocampal region CA1 (squares). Data were represented as percentage of neuroprotection, defined as the percentage to reach the control value (defined as 100%) from post-ischemic value without treatment (defined as 0%). F2 was administered (ranging from 0.0 to 0.1 mg/kg) by an intravenous injection at the onset of reperfusion after cerebral ischemia. The maximal effect (81%) was reached at a concentration of 0.05 mg/kg, with a half effective concentration of 0.015 mg/kg, in cortex; and a maximal effect (35%) at 0.05 mg/kg, and a half effective concentration of 0.025 mg/kg in CA1.

Previous results obtained for F2 efficacy assays (dose range 0.0-0.1 mg/kg) are represented here as a percentage of neuroprotection for each concentration tested. In FIG. 4, 0% neuroprotection was assigned to the cell damage or cell death (by FJB or TUNEL assays, respectively) obtained for the non-treated group. 100% neuroprotection stands for the complete absence of cell damage or cell death. This figure permits the evaluation of the neuroprotective activity of compound F2 in a dose response graph.

Conclusions

Efficacy curve for F2 (dose/response curve) at concentrations 0.0, 0.01, 0.025, 0.05 and 0.1 mg/kg administered by intravenous injection immediately after post-ischemic reperfusion shows that F2 treatment induced a significant neuroprotection against damage produced by cerebral ischemia in a concentration range between 0.05 and 0.1 mg/kg, being its highest effect at 0.05 mg/kg.

EXAMPLE 3

Therapy Window Study of F2 in Transitory Global Cerebral Ischemia

This assay has been performed and developed in the experimental model of global cerebral ischemia. The variables quantified to evaluate de neuroprotection of F2, neurological deficit score (NDS) and neuronal death and apoptosis in brain sections, were performed as described in Example 2.

After unblinding, data obtained for F2 administered at 0.05 mg/kg by intravenous injection at different times of reperfusion (1 h, 3 h, 6 h and 48 h) were analysed. Analysis of results included neuronal damage and death, and a functional test to which the animals were subjected prior to sacrifice. All the results were obtained 5d after post-ischemic reperfusion in a model of global cerebral ischemia. Data were compared to the group treated at reperfusion onset (0 h).

Analysis of Neuronal Death

Administration of F2 (0.05 mg/kg) significantly decreased neuronal death, as observed with Fluoro-Jade B staining, in the administration time points evaluated between 0 and 6 h after reperfusion, when compared to the vehicle group. This effect is observed in both hippocampal CA1 and cortical regions. In the cortex, a significant reduction in neuronal death can be observed when F2 was administered later than 6 h after the reperfusion onset (FIG. 6). When administered 48 h after reperfusion, F2 did not afford a significant decrease in the neuronal damage, although the values obtained were slightly reduced compared to the ones obtained in the vehicle group (FIG. 6).

Analysis of Neuronal Apoptosis

Neuronal apoptosis induced by ischemia was detected by TUNEL assay. Vh group corresponds to the vehicle-treated control group, which was administered saline. A significant reduction of apoptosis is observed when treated with F2, which reaches its maximum effect when administered between 0-3 hours after the onset of the reperfusion. When F2 was administered at 6 h after reperfusion, the effect of F2 on apoptosis was significant in both hippocampus and cerebral cortex. Finally, when administered at 48 h after reperfusion, F2 did not afford a significant decrease in the apoptosis, although the values obtained were slightly reduced compared to the ones obtained in the vehicle group. In the pictures, a significant reduction of apoptosis can be observed when animals are treated with F2 at 3 or 6 h after reperfusion (representative images of the results obtained in cerebral cortex) (FIG. 5).

Functional Test

Figure 7:
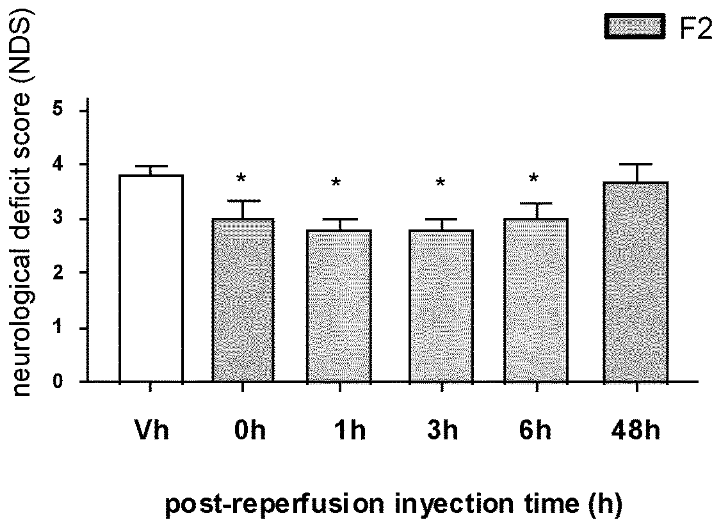
FIG. 7. In this figure, an improvement in the neurodeficit score (NDS) outcome is observed in the animals treated with F2, with significant differences compared to the vehicle group, when F2 was administered at the onset of reperfusion or 1-6 hours after reperfusion.

Animals were subjected to a functional test before sacrifice in order to quantify their potential disability. In this test, a series of variables related to the general state of the animal (breathing, coordination, aspect, etc.) were assigned a mark corresponding to the degree of severity by which that variable is affected. The sum of the mark obtained accounts for the neurological deficit score (NDS), which represents the general consciousness and neurological activity of the animal (0, healthy animal; 10, animal had a depressed level of consciousness). In FIG. 7, an improvement in the animal treated with F2 was observed with significative differences to the vehicle group when administered 0-6 hours after reperfusion. When administered 48 h after reperfusion, F2 treatment did not improve the NDS.

Conclusions

Treatment with steronitrone F2, administered between the onset of reperfusion and 6 h after onset, induces a significant decrease of neuronal damage and apoptosis, while improving the neurological deficit produced by cerebral ischemia, when compared to animals administered with vehicle.

Compound F2 induces a neuroprotective effect when administered within a therapeutic window starting at reperfusion until 6 h after onset of reperfusion.

In FIGS. 5 and 6, it can be observed that the maximum neuroprotective effect is achieved when F2 is administered 0-3 h after reperfusion onset. This effect decreases when F2 is administered 6 h after onset of reperfusion; when the compound is administered 48 h after reperfusion the effect on neuroprotection is no longer statistically significant.

The kinetics of the effect found corresponds to a particular mechanism of action. F2 is supposed to act through the inhibition of cellular damage during the first hours after the reperfusion, most likely acting on radical species and (hyper)oxidation-driven cellular alterations. These alterations are produced only in the first hours of re-oxygenation of the ischemic cerebral tissue. Once the tissue has recovered normal blood-flow and cellular homeostasis, damaging mechanisms are no longer active, hence, F2 compound lacks a therapeutic target through which it could exert its (neuroprotective) biological activity.

As a note/observation to the experimental methodology, data of each experimental group were normalized to each vehicle control group.

EXAMPLE 4

Long-term Study of F2 Efficacy in Transitory Global Cerebral Ischemia

This example has been performed and developed in the experimental model of global cerebral ischemia as described in example 2.

The results shown herein correspond to animals treated with compounds F2 or NXY059 administered by intravenous injection at the onset of reperfusion after cerebral ischemia, evaluating neuronal loss in brain sections 11 weeks after treatment. In addition, animal behaviour was evaluated before sacrifice for the neurological evolution evaluation.

Analysis of Neuronal Death

In previous experiments, neuronal damage and apoptosis produced by the ischemic episode was determined by Fluoro-Jade B and TUNEL assays at 5 days after post-ischemic reperfusion in a model of global ischemia. In this example, we wanted to evaluate the damage or apoptosis of neurons 11 weeks after the ischemic episode to assess the long-term effect of F2 treatment and to compare this effect to the one of untreated animals and animals treated with NXY059. During this time-period, damaged or dead cells were naturally reabsorbed by the brain parenchyma and therefore not observed after Fluoro-Jade B or TUNEL assays. Because of this, a new experimental strategy had to be used, based on the staining of viable neurons and its quantification in the areas of the brain more vulnerable to the ischemic episodes such as the hippocampal CA1 region. S6 ribosomal protein (in red), a constitutive protein present in the cytoplasm of neurons, was selected as the marker off cell viability. With this approach, we were able to observe whole neurons, indicating proper cell viability, in brain sections of healthy animals (see control panel of FIG. 8).

Figure 8:
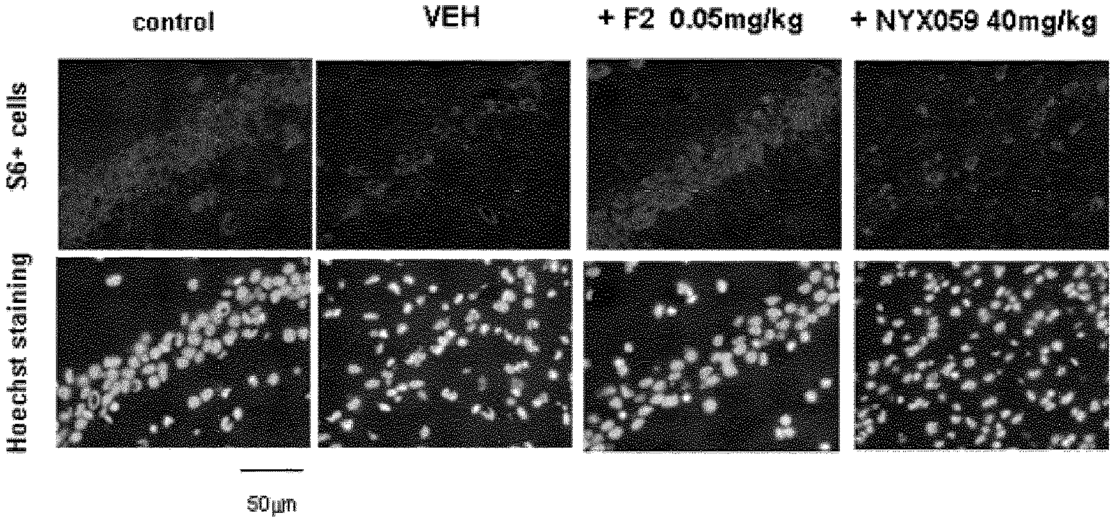
FIG. 8. F2 preserves neuronal cells in the hippocampal CA1 region three months after transient ischemia. Brain sections from control and untreated (vehicle) or F2- and NXY-059-treated ischemic animals 11 weeks (77 days) after reperfusion following ischemia (R77d, vehicle, +F2 and +NXY059, respectively) were used after fixation for cell detection. Neurons were labelled with anti-protein S6 antibody and X-red-secondary antibody and visualized by fluorescence microscopy (in red) and cells were also stained with Hoechst dye (in blue). The images are representative results of the hippocampal CA1 (CA1) regions.

In FIG. 8, viable neurons in CA1 hippocampal region 11 weeks after reperfusion were stained with S6 protein (in red, panels healthy control, and vehicle (VEH)-, F2- or NXY059-treated animals). In the figure, a drastic reduction in the S6-positive cells can be observed for vehicle- and NXY-059-treated animals compared to a healthy (control) or F2-treated animals.

Figure 9:
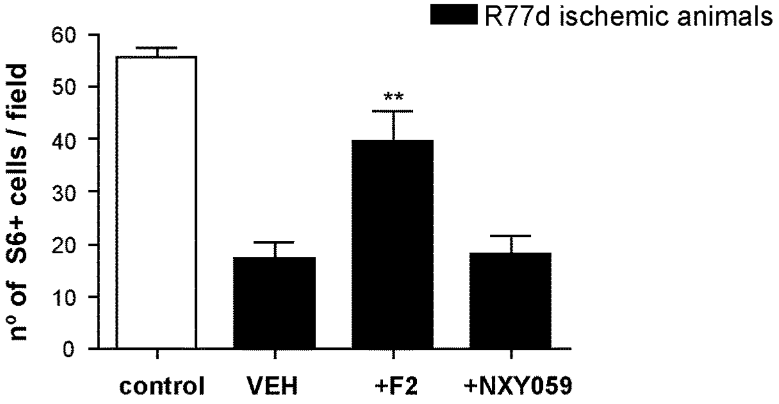
FIG. 9. S6-positive cells as in FIG. 8 were counted in CA1 fields (bar graph). Data from 6 independent animals per group were represented as means±SEM. *$p<0.05$, and **$p<0.01$, compared with control by Dunnett's post-test after ANOVA.

FIG. 9 represents the quantification results of viable neurons stained with S6, which were counted in a particular field of vision from the CA1 region of the hippocampus. Vehicle (VEH)-treated group represents the data of the animals with cerebral ischemia treated with the vehicle (ischemia control group). F2 treatment significantly preserves neuronal viability, reducing dramatically neuronal loss after ischemia at long-term.

Behavioural Tests

As mentioned above for neuronal damage/death, the functional tests used to evaluate neurological deficit 5 days after the ischemic episode are not adequate to evaluate long-term neurological deficit. Animals may recover from their initial functional deficits due to the inherent plasticity of the nervous system inherent, thus not showing any evident symptoms on these tests. However, this lack of symptomatology on the long term on these specific tests does not necessarily mean that there aren't any long-term sequalae from the insult. For this reason, alternative tests, directed towards the assessment of long-term effects rather than short-term effect were used in this experiment. These tests include evaluation of spatial memory, orientation, curiosity, behaviours that have been shown to be affected in the long-term in stroke patients.

Animals were subjected to two behavioural tests for their neurological evaluation prior to sacrifice in order to assess the exploratory activity and spatial recognition and memory; the Y-maze paradigm was used to assess these functions. For the first test, the animal is positioned in the centre of the maze, allowing free exploration for 8 minutes. Exploratory activity is quantified and represented as an activity index. For the assessment of the spatial recognition and memory, the number of times the animals alternate among the three arms (triad number) is evaluated and quantified as an alternation index. Lower activity and/or alternation indexes are indications of reduced curiosity and spatial memory and consequently higher neurological deficit.

—Exploration Activity Test

For the activity test, vehicle (VEH)-, F2- or NXY-059-treated groups were compared to the healthy animal's group. The results indicate that the VEH group had a statistically significant reduction in the activity index compared to the control group; this reduction in activity was considered, as mentioned above, a sign of higher neurological deficit. In contrast, the F2 group showed activity scores that were equivalent to those observed in the control group, clearly showing that treatment with F2 was able to restore the long-term deficits in activity caused by the ischemia-reperfusion insult. For the NXY059-treated group, the neurological deficit was similar to the one obtained for VEH, although no statistically significant differences were found when compared with the control group due to the great variability of the results in this experimental group.

—Spatial Recognition or Alternation Test

In the alternation test, vehicle (VEH)-, F2- or NXY059-treated groups were also compared to the healthy animals (control). As for the previous test, the VEH group showed a statistically significant reduction in the alternation index compared to the control group indicating that these animals had higher neurological deficits than the animals belonging to the control group. NXY059-treated group and, especially, F2-treated group ameliorated this deficit, resulting in no significant differences when compared to the scores of the control group, as it was the case for the activity index, the group of animals treated with NXY059 showed great variability in their response.

Conclusions

As shown by S6 protein staining, a period of cerebral ischemia of 15 min followed by reperfusion (VEH group or ischemia control) had a great effect on cell survival of neuronal cells in the CA1 region of the brain hippocampus, region intimately related to short-term memory and spatial memory. This effect was evaluated 11 weeks after the ischemia, when endogenous neurorepair processes have already finished.

Treatment with F2 administered after post-ischemic reperfusion induced a significant neuronal preservation against damage produced by cerebral ischemia. Remarkably, F2-treated neurons from CA1 hippocampal region were similar in number and morphology to hippocampal neurons of healthy animals (control).

In contrast, treatment with NXY-059 did not recover the damage observed, as can be seen by the complete disappearance of layers of neurons, similar to the ischemia control group (VEH).

Therefore, compound F2 induces neuroprotection against ischemic brain damage, resulting in a situation near to a non-ischemic episode. F2-treated animals showed better behavioural performance, both in activity and spatial memory assessment, than ischemic animals (VEH) or NXY059-treated, without finding significant differences to the healthy animals.

EXAMPLE 5

Efficacy Studies of F2 in an In Vivo Model of Transitory Focal Cerebral Ischemia and Comparison with NXY-059

Methods

Animal model of focal cerebral ischemia. Transient occlusion of a distal branch of the middle cerebral artery (tMCAO) was induced in male C57BL/6 mice (9-12-week-old, Charles River). The animals were housed in a light/dark cycle (12 h), humidity and temperature (22±2° C.) controlled environment with food and water available ad libitum. Briefly, mice were anesthetized with 4% isoflurane for induction and 1.5-2% isoflurane for maintenance (in 79% N2/21% 02). After drilling a small hole on the temporal bone, the middle cerebral artery (MCA) was compressed for 60 min with a 30-G needle using a micromanipulator. During the surgery, body temperature was maintained at 37.0±0.5° C. using a homoeothermic blanket and CBF was monitored using laser-Doppler flowmetry to confirm MCA occlusion. Buprenorphine (0.05-0.1 mg/kg) was administered subcutaneously immediately before the procedure. A total of 33 mice were subjected to tMCAO according to the design of the study. We performed a power analysis to determine sample size [significance level set at 0.05, the power set at 0.8 (80%)] resulting in 8 animals per experimental group. Surgical inclusion criteria: a reduction in blood flow to <25% of baseline value during ischemia period, and a recovery of 75% of baseline value in the reperfusion period. Animals that met the following criteria were excluded: (i) Animals that failed to meet the inclusion criteria explained above (2 mice); and (ii) animals that died during the induction of middle cerebral artery occlusion (MCAO) (2 mice). Mice were randomly assigned using a randomization software to the following experimental groups (n=9 per group): vehicle (saline-EtOH 90:10 vol/vol), F2 (0.05 and 0.1 mg/kg) and NXY-059 (40.0 mg/kg). The treatments were administered intraperitoneally at the onset of reperfusion period by an investigator blinded to the experimental condition. All procedures were approved by the local Animal Care Committee and were conducted in compliance with ARRIVE guidelines and the Spanish legislation and in accordance with the Directives of the EU.

Motor-Deficit Evaluation, Grip Strength Test.

Motor functional test was performed at 1 day before surgery and 24 h and 48 h after tMCAO to evaluate ischemic outcomes and monitor motor function by a blinded researcher to experimental conditions. Grip strength test is designed to assess the maximum force displayed by the mouse forelimbs (in grams) using a metallic grid connected to a force sensor (Bioseb). A total of 6 trials were conducted for each test and the strength value was calculated as the mean of them.

Infarct Volume Evaluation.

The size of infarction was evaluated at 48 h after MCAO using 2,3,5-tetrazolium chloride (TTC) staining. 60 Mice were sacrificed by transcardiac perfusion with ice-cold saline under deep anaesthesia. Brains were removed and cut into 1-mm-thick coronal sections and stained with 2.5% of TTC in saline for 20 min at room temperature. The analyses were performed in a blinded manner. The infarct areas were measured using the Image-J software and the infarct volume was determined by linear integration of the measured lesion areas and distances over the sections. In order to avoid brain oedema effects, infarct area was corrected by the ratio of the area of the ipsilateral and the contralateral hemisphere. Treatment information has remained blind during the performance of the experiment.

Results

Functional Test

Figure 10:
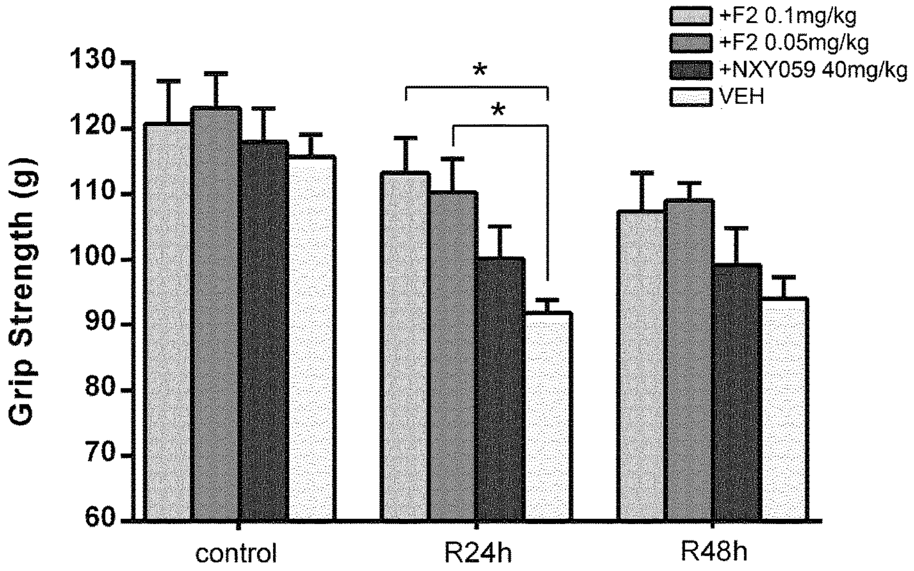
FIG. 10. Improvement of functional outcome by F2 treatment after transient middle cerebral artery occlusion (tMCAO). Functional motor deficit was evaluated by grip strength test. Administration of F2 (0.05 or 0.1 mg/kg) at the onset of the reperfusion, but not NXY-059 (40 mg/kg), improved grip strength values 24 h and 48 h after reperfusion (R24 h and R48 h) after transient middle cerebral artery occlusion (tMCAO). Grip strength values corresponding to presurgery animals (control) were showed. *$p<0.05$ and **$p<0.01$ compared with vehicle (VEH) by Bonferroni's post-test after two-way ANOVA. Results represent the means±SE of 9 independent animals; error bars indicate SE.

Analysis of the results obtained for the grip strength test shows statistically significant differences with a p-value of p=0.0015 among all the experimental groups tested (2-way ANOVA). Pair analysis shows significant differences between 0.1 mg/kg F2 treatment and control vehicle (VEH) (113.2±5.35 vs 91.76±2.00) and between 0.05 mg/kg F2 and VEH (110.2±5.14 vs 91.76±2.00) 24 hours after reperfusion (FIG. 10).

Infarct Volume Analysis

Figure 11:
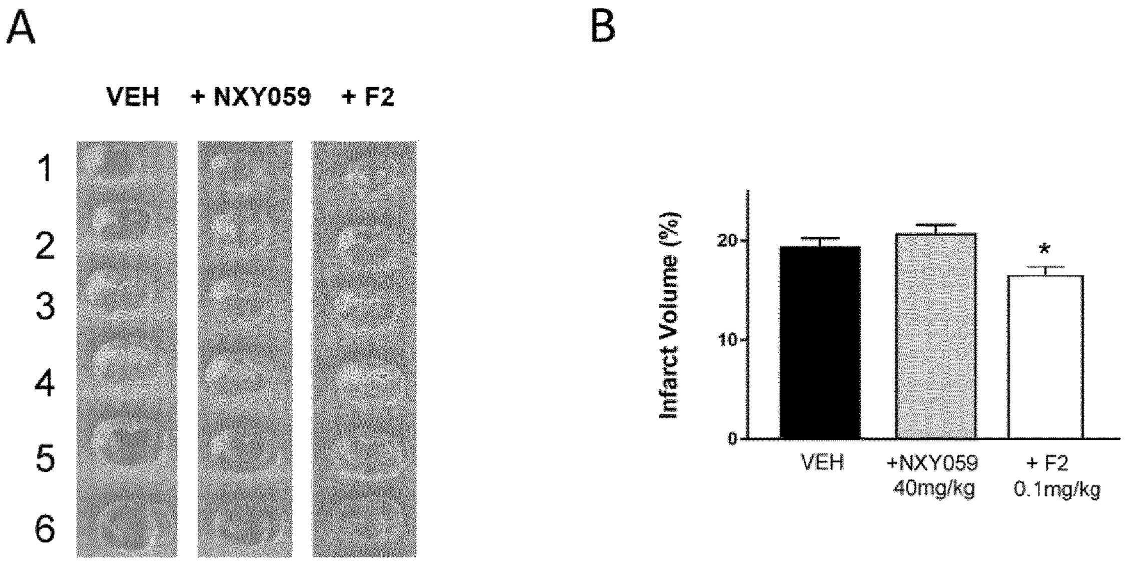
FIG. 11. F2 administration reduces infarct size after transient focal ischemia (tMCAO). (A) Six coronal sections (1 mm each) of the rostro-caudal axis from vehicle-, F2-, and NXY-059-treated animals after tMCAO (VEH, +F2, and +NXY059, respectively) were stained with TTC at 48 h of reperfusion after ischemia to evaluate the infarct size. Representative images of TTC staining are shown. F2 treatment (0.1 mg/kg) decreased infarct volume (B) compared with vehicle treatment (28.88±2.37 mm3 for VEH). Results represent the mean±SE of 9 independent animals; error bars indicate SE *$p<0.05$, *$p<0.01$, and *$p<0.001$ compared with vehicle by Bonferroni's post-test after ANOVA.

Analysis of the infarct volume shows statistically significant differences among the different experimental groups (p=0.0138, 1-way ANOVA). Treatment used in experimental group 0.1 mg/kg F2 significantly decreases (p<0.05) infarct volume in a 20.27% respect to NXY059 and 15.20% respect to control VEH. The infarct volume values for each experimental group (as percentages) are the following: Group F2, 16.24±0.85 (n=9); Group NXY059, 20.37±0.93 (n=10); Group control VEH, 19.15±1.08 (n=9) (FIG. 11).

Conclusions

Treatment with F2 decreases the loss of motor function when compared to vehicle treatment in the functional test. Treatment with F2 significantly reduces infarct volume when compared to vehicle and to NXY059 treatment.

EXAMPLE 6

Effect of Cholesteronitrone F2 in an In Vivo Model of Permanent Focal Cerebral Ischemia Preliminary in vitro and in vivo studies have shown the antioxidant and neuroprotective potential of F2. Here, the neuroprotective efficacy of this nitrone has been assayed in a model of permanent focal cerebral ischemia in mice. The permanent ischemia was performed by the permanent occlusion of the middle cerebral artery (MCA) at distal level respect the Willis polygon. In mice, this model produces a well-defined brain damage restricted to the cerebral cortex with involvement of the sensory maps of the front and rear limbs and the cortex in “barrel”, avoiding the much more variable effects of reperfusion ischemia models. In addition, since most stroke patients do not receive anti-thrombolytic therapies (pharmacological or endovascular) or experience spontaneous reperfusion, scientific meetings such as STAIR (Stroke Treatment Academic Industry Roundtable) have recommend this type of permanent models to assay the effect of different preclinical strategies before the clinics (Albers et al. 2011, Stroke, 42, 2645-2650; 10.1161/STROKEAHA.111.618850).

Results

Infarct Volume Analysis

Figure 12:
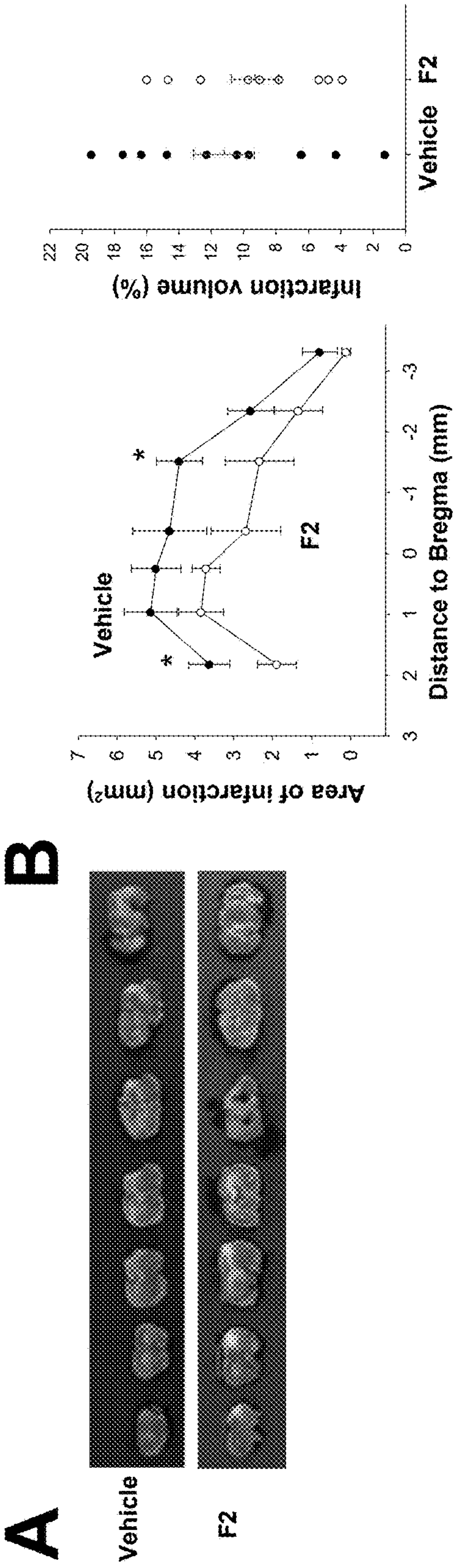
FIG. 12. Histological assessment to determine the infarct area after permanent MCA occlusion (pMCAO) in mice treated with F2. (A) Representative images of TTC-stained coronal sections from treated (F2) and non-treated (vehicle) mice 48 hours after permanent occlusion of MCA. The infarct area (in white) is mainly localized to cortical regions in areas affecting the somatosensory territory and, to a lesser extent, the motor cortex. (B) The left panel shows the regional distribution of the area of infarction along the rostrocaudal axis as measured from bregma. The right panel shows the infarct volume after focal ischemia induced by MCA occlusion. The infarct volumes are represented as percentages of the total volume of the contralateral non-damaged hemisphere. The data are shown as the means the standard error of the mean (SEM). The asterisks denote significant differences between groups for particular distance to Bregma (two-way ANOVA followed by Tukey's test; *$p<0.05$).

In this example, the intraperitoneal administration of F2 (dose: 0.1 mg/kg) at 2 and 12 hours after unilateral MCA occlusion (right hemisphere) produced a significant recovery of stroke animals that was not seen in stroke animals merely injected with vehicle (no F2 compound). The positive effect of F2 was first associated with a reduction in the extension damage examined by triphenyltetrazolium chloride (TTC) staining. Thus, F2-treated animals showed a lower infarcted area respect non-treated animal (FIG. 12).

Functional Studies

Figure 13:
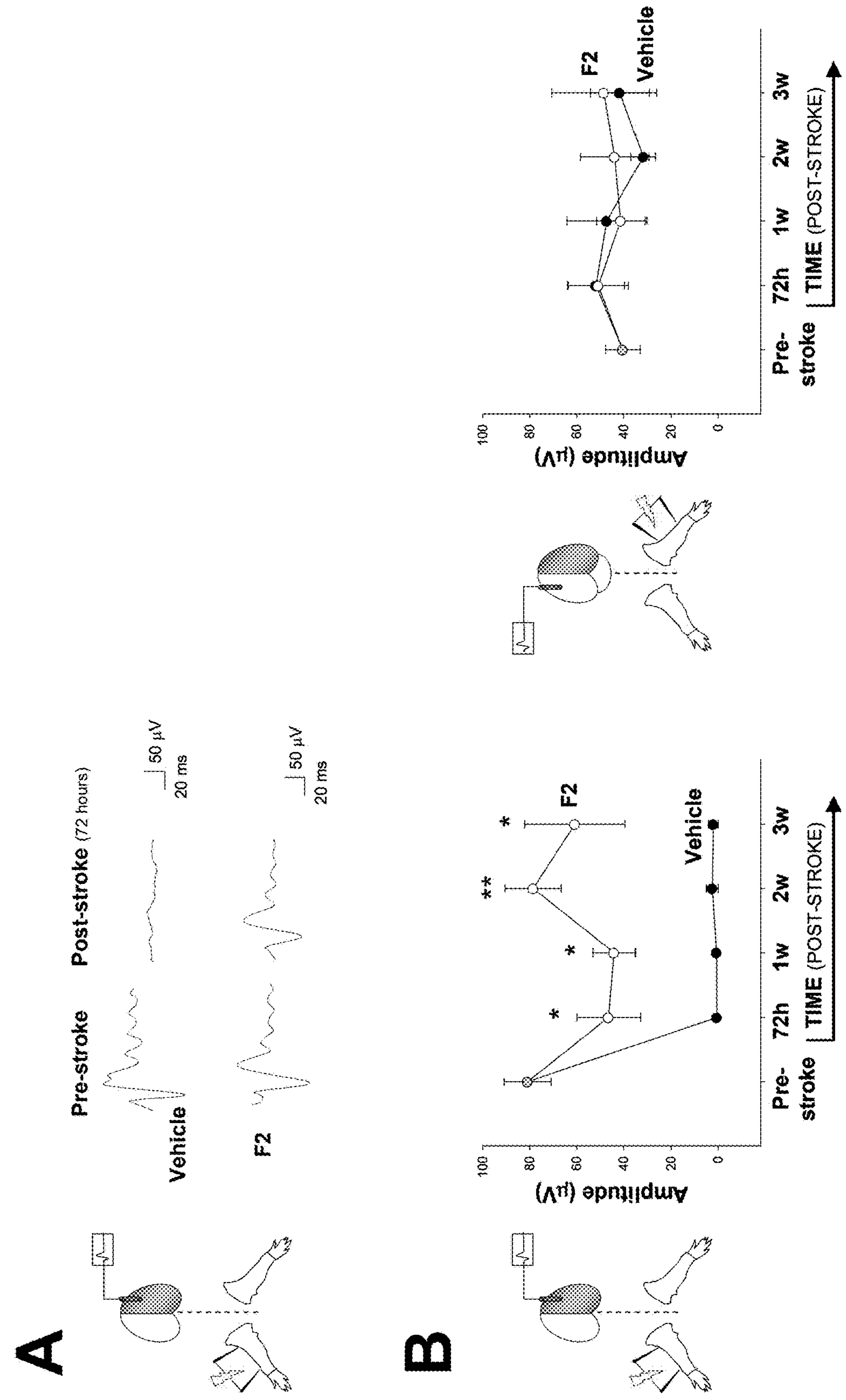
FIG. 13. Evaluation of functional brain territory in stroke mice with pMCAO and treated with F2. (A) Representative somatosensory evoked contralateral potentials recorded before and 72 hours post-stroke in treated (F2) and non-treated (vehicle, control) mice. F2 was administered at 2 and 12 hours after MCA ligation. The cartoon on the left shows the position of recording electrode in the right hemisphere (damaged) in relation with the stimulated left forepaw. In both groups, the electrical stimulus was twice the current level necessary to obtain a supramaximal motor response, typically 1-2 mA. (B) Amplitude of evoked activity in the somatosensory cortex (forepaw sensory field) in the infarcted (left panel) and non-infarcted (right panel) hemispheres of non-treated (vehicle) and treated (F2) mice over time after stroke. The cartoons show the position of recording electrode in relation with the stimulated forepaw. Data are presented as the means±SEM. For every time point analysed, the black asterisks denote significant differences between non-treated (vehicle) and treated (F2) mice (two-way ANOVA followed by Tukey's test; *$p<0.05$, **$p<0.05$).

The neuroprotective effect of F2 was translated into a higher functional preservation of cortical territory examined by the recordings of somatosensory evoked potentials (FIG. 13). As soon as 72 hours after stroke the non-treated animals (vehicle) showed a strong loss of cortical activity in the right somatosensory cortex (forepaw field) in response to left forelimb contralateral stimulation. This lack of responsiveness remained stable during the time period of the study (3 weeks). In the same manner, in non-treated animals, the stimulation of the right forelimb caused a normal response in the non-damage left hemisphere, similar to the pre-stroke condition. Under the same stimuli conditions, mice treated with F2 showed in the damaged hemisphere (right) a preserved cortical response at 72 hours post-stroke and during the total time of study, reaching voltage values similar to the pre-stroke condition at 2 and 3 weeks respectively. In the non-damaged hemisphere, the voltage response in the time period of study was similar to the pre-stroke condition. These results suggest that in F2-treated mice the amount of functional brain territory is significantly higher than in non-treated animals. F2 is protecting the brain from the detrimental effects of unilateral permanent occlusion of MCA.

Figure 14:
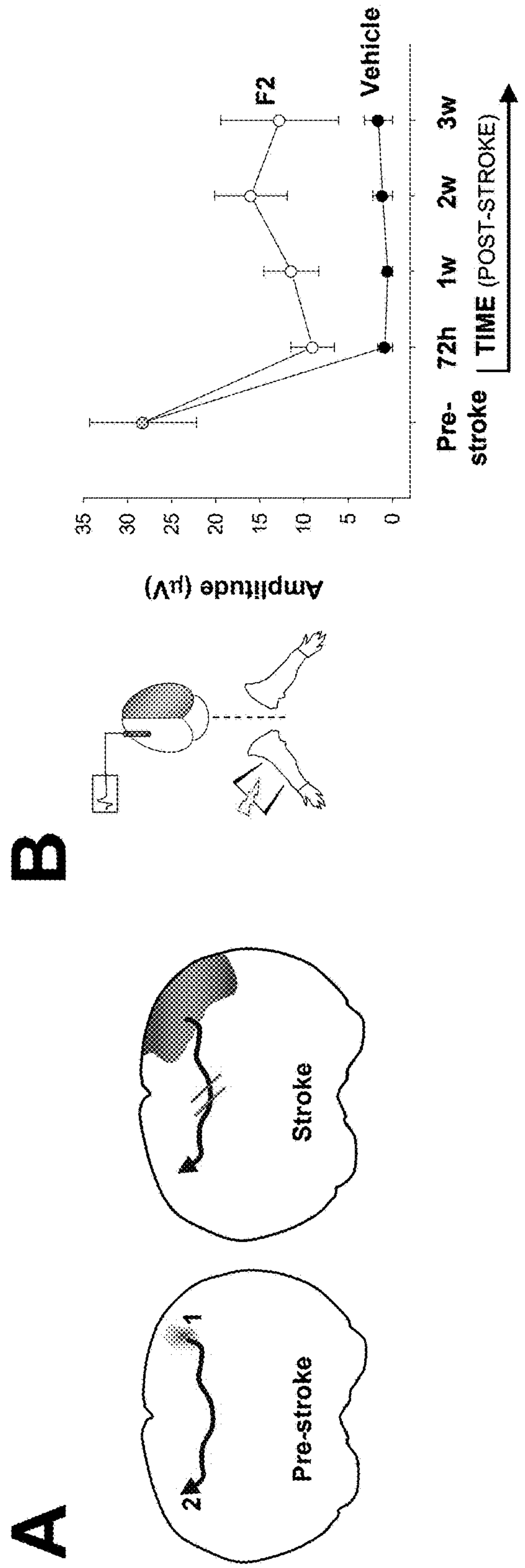
FIG. 14. Ipsilateral activity in stroke mice with pMCAO and treated with F2. (A) The cartoon shows the main fundaments of ipsilateral response in the context of forepaw somatosensory response. After forelimb stimulation a focus of activity emerges in the contralateral response [1]. Neuronal bodies from this somatosensory area project in homologous/nearby regions of the opposite hemisphere generating an ipsilateral potential [2]. After unilateral stroke (grey spot in the cartoon), the ipsilateral potential can be suppressed in the non-infarcted hemisphere as we have previously described (PMID: 26661150) (B) The cartoon on the left shows the position of recording electrode in the left hemisphere (non-damaged) in relation with the stimulated forepaw (left). (C) Amplitude of somatosensory evoked activity (forepaw sensory field) in the non-damaged hemisphere of non-treated (vehicle) and treated (F2) mice over time after stroke and F2 or vehicle administration.

The analysis of ipsilateral potentials corroborated these findings. In non-damage mice, forepaw stimulation produces an initial response in the contralateral hemisphere. This contralateral response is conducted and transmitted by interhemispheric fibres (corpus callosum) to the opposite hemisphere generating a late ipsilateral potential (same side of stimulated forepaw) (FIG. 14A). Although after stroke the magnitude of ipsilateral potentials was reduced in both groups of animals (F2 and vehicle), these potentials were more preserved in F2 mice than in non-treated animals (FIG. 14B). In fact, in treated animals (F2) the temporal course of ipsilateral response followed the dynamics of contralateral response determined in the damaged hemisphere (FIG. 13B, left panel). The magnitude and time course of ipsilateral activity is highly compatible with the major preservation of contralateral response in the damaged hemisphere of F2-treated animals previously described (FIG. 13).

Conclusions

The cholesteronitrone F2 significantly reduces infarct volume in F2-treated animals with permanent cerebral ischemia. The neuroprotective effect of F2 was translated into a higher functional preservation of cortical territory examined by the recordings of somatosensory evoked potentials, effect that could be observed after three weeks of F2 treatment.

EXAMPLE 7

Therapy Window Study of Nitrone NXY-059 in Transitory Global Cerebral Ischemia Results This assay has been performed and developed in an experimental model of global cerebral ischemia as described in Example 2. The variables quantified to evaluate de neuroprotection of NXY-059, including neurological deficit score (NDS) and neuronal death and apoptosis in brain sections, were performed as described in Example 3.

Data obtained for NXY-059 administered at 40 mg/kg by intravenous injection at the onset of reperfusion (0 h) or at different times following reperfusion (1 h, 3 h, 6 h and 48 h) were analyzed. Analysis of results included neuronal death and neuronal apoptosis, and a neurofunctional test performed in the animals prior to their sacrifice. All the results were obtained 5 d after post-ischemic reperfusion in the model of global cerebral ischemia. Data were compared to the group treated at reperfusion onset (0 h).

Analysis of Neuronal Death

Figure 15:
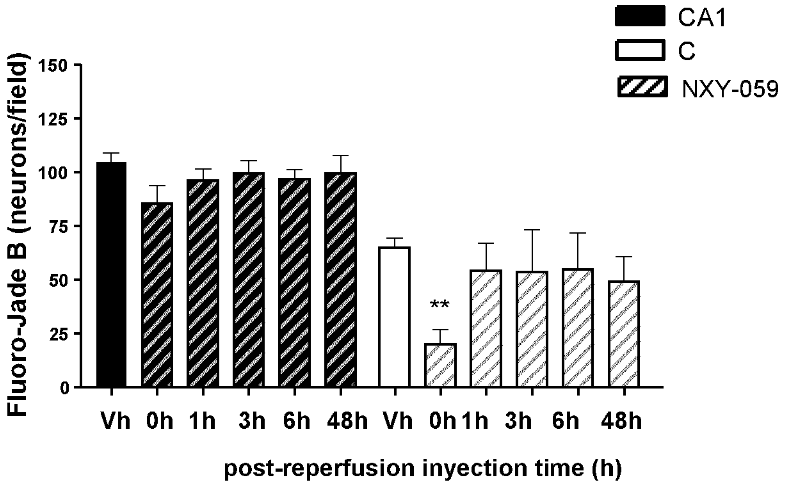
FIG. 15. Therapeutic window study of nitrone NXY-059. Brain sections from untreated (vehicle, Vh) or NXY-059 (40.0 mg/kg) treated ischemic animals were used for neuroprotection evaluation. Animals were treated with NXY-059 by an intravenous injection at the onset of reperfusion period (0h) or at 1 h, 3 h, 6 h or 48 h of reperfusion after cerebral ischemia. Neuronal death was quantified in brain sections in vehicle- and NXY-059-treated animals after fixation and staining with Fluoro-Jade B. Neuroprotection was determined by quantification of the decrease of neuronal death at 5 days after reperfusion following ischemia in the cerebral cortex (C, white bars) and hippocampal CA1 (black bars) regions and compared with control vehicle (Vh).

We compared the effect of F2 as indicated in Example 3 with nitrone NXY-059, a drug that has been extensively assayed in experimental ischemia in rats at doses ranging from 0.3 to 120 mg/kg (averaged dose, 42 mg/kg), showing neuroprotective properties (Bath, P. M.; Gray, L. J.; Bath, A. J.; Buchan, A.; Miyata, T.; Green, A. R. Effects of NXY-059 in experimental stroke: an individual animal meta-analysis. Br. J. Pharmacol. 2009, 157, 1157-1171) and tested in clinical trials (Fong, J. J.; Rhoney, D. H. NXY-059: review of neuroprotective potential for acute stroke. Ann. Pharmacother. 2006, 40, 461-471; Floyd, R. A.; Kopke, R. D.; Choi, C. H.; Foster, S. B.; Doblas, S.; Towner, R. A. Nitrones as therapeutics. Free Radical Biol. Med. 2008, 45, 1361-1374; Savitz, S. I. A critical appraisal of the NXY-059 neuroprotection studies for acute stroke: a need for more rigorous testing of neuroprotective agents in animal models of stroke. Exp. Neurol. 2007, 205, 20-25.). After 5 days of reperfusion following cerebral ischemia, NXY-059 administered at reperfusion onset (Oh) showed a lower neuroprotective effect (FIG. 15) compared with F2 in the results shown in Example 3 (FIG. 6), which also showed a significant and higher neuroprotective effect when it was administered between 1 and 6 h after reperfusion (FIG. 6). In contrast, NXY-059 did not induce a decrease in neuronal damage when administered 1-48 h after reperfusion (FIG. 15).

Analysis of Neuronal Apoptosis

Figure 16:
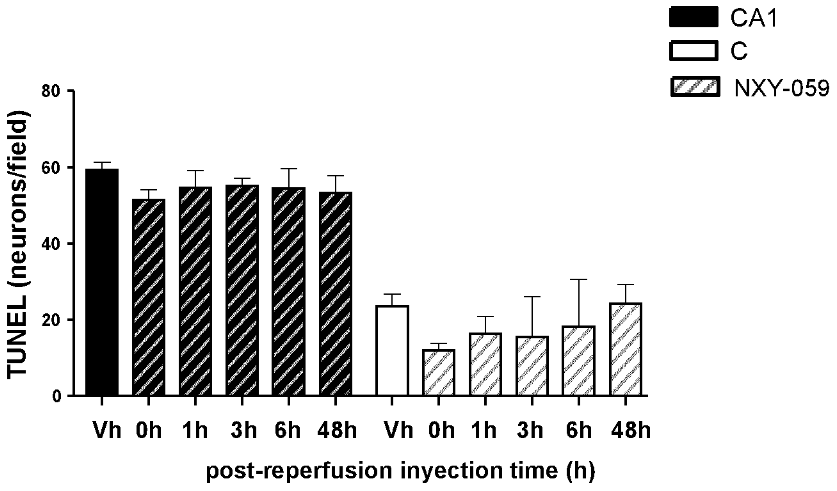
FIG. 16. Therapeutic window study of nitrone NXY-059. Analysis of neuronal apoptosis. This figure represents the neuronal apoptosis quantified in brain sections from vehicle- and NXY-059- treated animals (as in FIG. 15) after fixation and staining with TUNEL assay. Neuroprotection was determined by quantification of the decrease of neuronal apoptosis at 5 days after reperfusion following ischemia in the hippocampal CA1 (black bars) and cortical (C, white bars) regions.

Neuronal apoptosis induced by ischemia was detected by using a TUNEL assay. Vh group corresponds to the vehicle-treated control group, which was administered saline. In the previous results shown in Example 3, a significant reduction of neuronal apoptosis was observed when animals were treated with F2 between 0-6 hours after reperfusion following ischemia (FIG. 5). When NXY-059 was used for treatment and administered between 0 and 48 h after reperfusion, it did not afford a significant decrease in the neuronal apoptosis, although the values obtained at 0 h were lower than those obtained in the vehicle group (FIG. 16).

Functional Test

Figure 17:
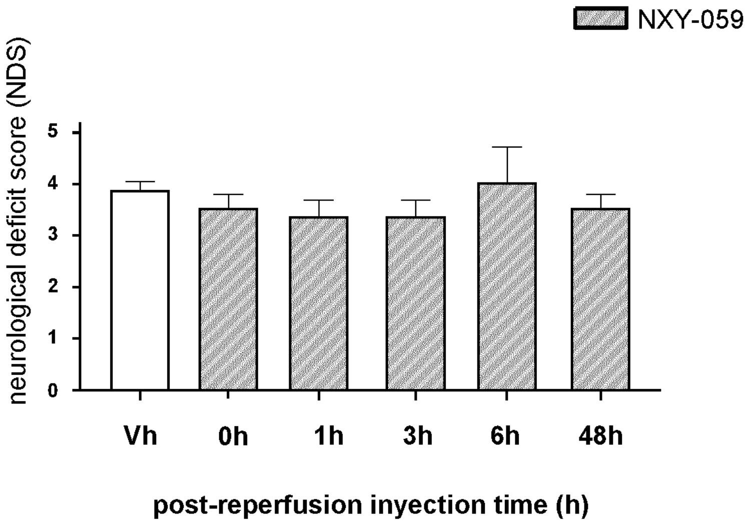
FIG. 17. In this figure, no significant improvement in the neurodeficit score (NDS) outcome was observed in the animals treated with NXY-059 compared with the vehicle group, when NXY-059 was administered in the therapeutic window study.

Animals were subjected to a functional test before their sacrifice in order to quantify their potential disability. With this test, neurological deficit score (NDS) was obtained as described in Example 3, where 0 is a healthy animal and 10 represents an animal with a depressed level of consciousness. In the bar graph, NXY-059 treatment did not improve the NDS, although the values obtained at 0-3 hours were slightly reduced to the ones obtained in the vehicle group (FIG. 17). In contrast, in the animals treated with F2 a significant difference compared with the vehicle group was observed when it was administered 0-6 hours after reperfusion, results showed in Example 3 (FIG. 7).

CONCLUSIONS

Treatment with nitrone NXY-059 only induced a significant decrease of neuronal damage administered at the onset of the reperfusion. On the contrary, steronitrone F2 administered between the onset of reperfusion and 6 h after, induced a significant decrease of neuronal death and neuronal apoptosis, as well as an improvement in the neurological deficit, when compared with the damage produced by cerebral ischemia in both untreated and NXY-059-treated animals. Thus, nitrone NXY-059 had a narrow therapeutic window compared to F2, which showed a neuroprotective effect within a therapeutic window until 6 h after the onset of reperfusion.

As a note/observation to the experimental methodology, data of each experimental group were normalized to each vehicle control group. Treatment information and experimental data were blindly performed throughout the study. All procedures were approved by the local Animal Care Committee and were conducted in accordance with the Directives of the EU.

The invention claimed is:

1. A method for treating permanent cerebral ischemia, the method comprising administering to a patient in need thereof a therapeutically effective amount of a pharmaceutical composition comprising steroidal nitrone E)-N-((8S,9S,10R,13R,14S,17R)-10,13-dimethyl-17-((R)-6-methylheptan-2-yl)-7,8,9,11,12,13,14,15,16,17-decahydro-1H-cyclopenta[a]phenanthren-3(2H,6H,10H)-ylidene) methanamine oxide (F2) or pharmaceutically acceptable salt thereof, wherein the administering occurs prior to reperfusion of the ischemic brain tissue, whether reperfusion would occur spontaneously or therapeutically.

2. The method of claim 1, wherein the composition includes pharmaceutically suitable excipients.

3. The method of claim 1, wherein administering is carried out intravenously.

4. The method of claim 1, wherein administering includes a dosage of the composition that is about 0.1 mg/kg.

5. The method of claim 1, wherein administering comprises two doses at about 2 hours and about 12 hours after arterial occlusion.

* * * * *